United States Patent
Verbinski et al.

(10) Patent No.: US 7,045,787 B1
(45) Date of Patent: May 16, 2006

(54) DENSITY DETECTION USING REAL TIME DISCRETE PHOTON COUNTING FOR FAST MOVING TARGETS

(75) Inventors: Victor Verbinski, La Jolla, CA (US); Scott Smith, San Diego, CA (US); Kenneth Valentine, deceased, late of Glen Ellen, CA (US); by Judith Maxwell, legal representative, Glen Ellen, CA (US); Jeffrey Adams, San Marcos, CA (US); Ryan Shyffer, San Diego, CA (US)

(73) Assignee: Science Applications International Corporation, San Diego, CA (US)

( * ) Notice: Subject to any disclaimer, the term of this patent is extended or adjusted under 35 U.S.C. 154(b) by 265 days.

(21) Appl. No.: 09/925,009

(22) Filed: Aug. 9, 2001

Related U.S. Application Data

(63) Continuation-in-part of application No. 09/398,547, filed on Sep. 17, 1999, now Pat. No. 6,507,025, which is a continuation-in-part of application No. 08/921,854, filed on Sep. 2, 1997, now abandoned, which is a continuation-in-part of application No. 08/546,999, filed on Oct. 23, 1995, now abandoned.

(51) Int. Cl.
*G01N 23/10* (2006.01)
*G01T 1/20* (2006.01)

(52) U.S. Cl. .............................. 250/358.1; 250/359.1; 250/360.1; 250/369; 378/57

(58) Field of Classification Search ............. 250/358.1, 250/360.1, 359.1, 309; 378/57, 197, 198, 378/51, 54, 55, 62
See application file for complete search history.

(56) References Cited

U.S. PATENT DOCUMENTS

| 3,124,679 A | 3/1964 | Tittman et al. ............ 250/43.5 |
| 3,780,291 A | 12/1973 | Stein et al. ................. 250/363 |

(Continued)

FOREIGN PATENT DOCUMENTS

GB  2 277 013 A  10/1994

OTHER PUBLICATIONS

U.S. Appl. No. 09/398,547, titled "Density Detection using Real Time Discrete Photon Counting for Fast Moving Targets," filed Sep. 17, 1999, relied on under 35 U.S.C. §120.

(Continued)

*Primary Examiner*—Albert Gagliardi
(74) *Attorney, Agent, or Firm*—Kilpatrick Stockton LLP

(57) ABSTRACT

A system for detecting and graphically displaying a contents of a fast-moving target object comprises: a radiation source, having a position such that at least a portion of radiation emitted from the radiation source passes through the fast-moving target object, the fast-moving target object having a variable velocity and acceleration while maintaining a substantially constant distance from the radiation source and being selected from the group consisting of: a vehicle, a cargo container and a railroad car; a velocity measuring device configured to measure the variable velocity of the fast-moving target object; a detector array comprising a plurality of photon detectors, having a position such that at least some of the at least a portion of the radiation passing through the target object is received thereby, the detector array having a variable count time according to the variable velocity and a grid unit size; a counter circuit coupled to the detector array for discretely counting a number of photons entering individual photon detectors, the counter circuit measuring a count rate according to a contents within the fast-moving target object; a high baud-rate interface coupled to the counter circuit for sending count information from the counter circuit at a rate fast enough to support real-time data transfer therethrough; and a processor coupled to the velocity measuring device and to the high-baud-rate interface, receiving count information from the high baud-rate interface and generating distortion-free image data in real time as a function of the count information and the variable velocity. A method for using the system is also disclosed.

3 Claims, 18 Drawing Sheets

U.S. PATENT DOCUMENTS

| | | | |
|---|---|---|---|
| 3,784,827 A | | 1/1974 | Calhoun |
| 3,790,785 A | | 2/1974 | Paolini et al. ......... 250/71.5 R |
| 3,808,444 A | * | 4/1974 | Schneeberger et al. ....... 378/57 |
| 3,835,324 A | | 9/1974 | Weigle ........................ 250/360 |
| 3,997,787 A | | 12/1976 | Fearon et al. ............... 250/359 |
| 4,047,036 A | * | 9/1977 | Smith et al. .................. 378/56 |
| 4,064,440 A | | 12/1977 | Roder ......................... 250/359 |
| 4,229,654 A | | 10/1980 | Arya et al. ............. 250/358 R |
| 4,251,726 A | | 2/1981 | Alvarez ...................... 250/302 |
| 4,255,659 A | | 3/1981 | Kaufman et al. ........... 250/370 |
| 4,366,382 A | | 12/1982 | Kotowski .................... 378/57 |
| 4,430,568 A | | 2/1984 | Yoshida et al. .......... 250/358.1 |
| 4,566,113 A | * | 1/1986 | Donges et al. ............... 378/57 |
| 4,598,202 A | | 7/1986 | Koechner ................... 250/366 |
| 4,599,740 A | | 7/1986 | Cable .......................... 378/57 |
| 4,697,594 A | | 10/1987 | Mayo, Jr. ................... 128/653 |
| 4,817,123 A | * | 3/1989 | Sones et al. .................. 378/98 |
| 4,873,708 A | * | 10/1989 | Cusano et al. ................ 378/19 |
| 4,893,015 A | | 1/1990 | Kubierschky et al. ...... 250/369 |
| 4,973,846 A | | 11/1990 | Lanza et al. ............. 250/385.1 |
| 5,065,418 A | | 11/1991 | Bermbach et al. |
| 5,091,924 A | | 2/1992 | Bermbach et al. ............ 378/57 |
| 5,151,588 A | | 9/1992 | Kiri et al. ................. 250/208.1 |
| 5,237,598 A | | 8/1993 | Albert ......................... 378/99 |
| 5,247,561 A | | 9/1993 | Kotowski .................... 378/87 |
| 5,379,334 A | | 1/1995 | Zimmer et al. ............ 378/98.2 |
| 5,464,013 A | | 11/1995 | Lemelson ................ 128/653.1 |
| 5,493,517 A | | 2/1996 | Frazier ....................... 364/564 |
| 5,493,596 A | | 2/1996 | Annis .......................... 378/57 |
| 5,541,856 A | | 7/1996 | Hammermeister .......... 364/552 |
| 5,638,420 A | | 6/1997 | Armistead ................... 378/57 |
| 5,642,393 A | * | 6/1997 | Krug et al. ................... 378/57 |
| 5,692,028 A | | 11/1997 | Geus et al. ................... 378/57 |
| 5,698,854 A | * | 12/1997 | Gupta ..................... 250/358.1 |
| 5,754,617 A | | 5/1998 | Itoh .............................. 378/4 |
| 5,764,683 A | | 6/1998 | Swift et al. ................... 378/57 |
| 5,838,759 A | | 11/1998 | Armistead ................... 378/57 |
| 5,870,449 A | * | 2/1999 | Lee et al. ..................... 378/57 |
| 5,903,623 A | | 5/1999 | Swift et al. ................... 378/57 |
| 5,910,973 A | | 6/1999 | Grodzins ..................... 378/57 |
| 5,936,249 A | | 8/1999 | Eisen et al. ............ 250/370.06 |
| 6,031,890 A | | 2/2000 | Bermbach et al. ............ 378/57 |
| 6,058,158 A | | 5/2000 | Eiler ........................... 378/57 |
| 6,255,654 B1 | | 7/2001 | Verbinski et al. ........ 250/358.1 |
| 6,542,580 B1 | | 4/2003 | Carver et al. ............... 378/580 |

OTHER PUBLICATIONS

U.S. Appl. No. 08/921,854, titled "Density Detection Using Discrete Photon Counting," filed Sep. 2, 1997, relied on under 35 U.S.C. §120.

U.S. Appl. No. 08/546,999, titled "Density Detection Using Discrete Photon Counting," filed Oct. 23, 1995 (now abandoned), relied on under 35 U.S.C. §120.

"SAIC's Vacis II to Search for Contraband at U.S. Borders—U.S. Customs Services Issues Contracts for 29 VACIS IIs" [online], Jul. 30, 1999 [retrieved on Apr. 30, 2002], 1 p., Retrieved from the Internet: http://www.laprensa-sandiego.org/archieve/july30/vacis.htm.

"Vehicle & Cargo Inspection System" [online], Xtek General Security Products, Copyright 2001 [retrieved on Apr. 30, 2002], 1 p., Retrieved from the Internet: http://www.x-tek.net/catalogue/general/vacis.shtml.

Emery, Gail Repsher, "SAIC Sells Imaging Systems to Customs Service" [online], Mar. 20, 2001 [retrieved on Apr. 30, 2002], 2 pp., Retrieved from the Internet: http://www.washingtontechnology.com/news/1_1/daily_news/16302-1.html.

"U.S. Customs Service Orders Nine Railroad VACIS Units—SAIC's VACIS Technology to Be Used for Rail Car Inspections at Major U.S. Rail Border Locations" [online], May 21, 2001 [retrieved on Apr. 30, 2002], 2 pp., Retrieved from the Internet: http://www.saic.com/news/may01/news05-21-01.html.

McBee, Christopher J., Bowlin, David W. and Orphan, Victor J., "Mobile Cargo Inspection Provides Improved Throughput Efficiency and Flexibility," *Port Technology International,* 4 pp.

Snell, Michael P., "Gamma–Ray Technology: The Practical Container Inspection Alternative," *Port Technology International,* 6 pp.

Richardson, Rex D., Verbinski, VIctor V. and Orphan, Victor J., "New VACIS Applications and Performance Enhancements," 16 pp.

"VACIS—SAIC's Vehicle and Cargo Inspection Systems," 10 pp.

"U.S. Customs Service Inspectors Seize 2,362 Pounds of Marijuana at El Paso Port of Entry" [online], Mar. 8, 2002 [retrieved on May 22, 2002], 1 p., Retrieved from Internet: http://www.customs.gov/hot-new/pressrel/2002/0311-00.htm.

"U.S. Customs Service Inspectors Seize 234 Pounds of Cocaine at Presidio Port—High Tech Tools Help Pinpoint Drug Load" [online], Feb. 13, 2002 [retrieved on May 22, 2002], 1 p., Retrieved from Internet: http://www.customs.gov/hot-new/pressrel/2002/0215-03.htm.

"U.S. Customs Seizes $18 Million Load of Marijuana-Encased Cocaine From Commercial Bus in Eagle Pass" [online], Jul. 2, 2001 [retrieved on May 22, 2002], 1 p., Retrieved from the Internet: http://www.customs.gov/hot-new/pressrel/2001/0702-01.htm.

"Customs Seizes Marijuana from Two Commercial Trucks" [online], May 21, 2001 [retrieved on May 22, 2002], 1 p., Retrieved from the Internet: http://www.customs.gov/hot-new/pressrel/2001/0523-02.htm.

"U.S. Customs Service Inspectors Make Record Seizure at Santa Teresa Port—More Than 2½ Tons of Marijuana Confiscated" [online], Feb. 4, 2002 [retrieved on May 22, 2002], 1 p., Retrieved from the Internet: http://www.customs.gov/hot-new/pressrel/2002/0207-01.htm.

"U.S. Customs Service Inspectors Locate 1,700 Pound Marijuana Load—Seizure is One of Five Made at Nogales Tuesday" [online], Jan. 30, 2002 [retrieved on May 22, 2002], 1 p., Retrieved from the Internet: http://www.customs.gov/hot-new/pressrel/2002/0207-00.htm.

"U.S. Customs Inspectors in South Texas Seize $5.3 Million in Narcotics Over Veteran's Day Weekend" [online], Nov. 13, 2001 [retrieved on May 22, 2002], 1 p., Retrieved from the Internet: http://www.customs.gov/hot-new/pressrel/2001/1115-01.htm.

"U.S. Customs Inspectors Seize Over a Ton of Marijuana in Bus at Lincoln–Juarez Bridge, Two Arrested" [online], Nov. 6, 2001 [retrieved on May 22, 2002], 1 p., Retrieved from the Internet: http://www.customs.gov/hot-new/pressrel/2001/1106-00.htm.

"U.S. Customs Inspectors Seize 181 Pounds of Cocaine at Hidalgo/Pharr Port of Entry in Past Few Days" [online], Oct. 3, 2001 [retrieved on May 22, 2002], 2 pp., Retrieved from the Internet: http://www.customs.gov/hot-new/pressrel/2001/1004-01.htm.

"U.S. Customs Seizes Significant Marijuana Load in Bus at Roma Port of Entry" [online], Aug. 8, 2001 [retrieved on May 22, 2002], 1 p., Retrieved from the Internet: http://www.customs.gov/hot–new/pressrel/2001/0808–02.htm.

"Customs Inspectors in Naco and Nogales Stop Commercial Trucks Loaded With Dope—Seizures Net More Than 2,300 Pounds of Marijuana" [online], Jul. 20, 2001 [retrieved on May 22, 2002], 1 p., Retrieved from the Internet: http://www.customs.gov/hot–new/pressrel/2001/0720–02/htm.

"U.S. Customs Service Makes Record Drug Seizure At Santa Teresa Port of Entry" [online], Jul. 13, 2001 [retrieved on May 22, 2002], 1 p., Retrieved from the Internet: http://www.customs.gov/hot–new/pressrel/2001/0718–01.htm.

"U.S. Customs Inspectors Locate 1,296 Pound Marijuana Load in Commercial Truck at Nogales Port" [online], May 18, 2001 [retrieved on May 22, 2002], 1 p., Retrieved from the Internet: http://www.customs.gov/hot–new/pressrel/2001/0518–04.htm.

"U.S. Customs Seizes Ton of Marijuana in Back–To–Back Seizures at World Trade Bridge Last Night—Inspectors Have Seized 4,407 Pounds at World Trade Bridge in Past Week" [online], May 11, 2001 [retrieved on May 22, 2002], 1 p., Retrieved from the Internet: http://www.customs.gov/hot–new/pressrel/2001/0514–01.htm.

"U.S. Customs Inspectors Seize More Than Half–A–Million in Cash in Roma, One Arrested" [online], May 9, 2001 [retrieved on May 22, 2002], 1 p., Retrieved from the Internet: http://www.customs.gov/hot–new/pressrel/2001/0509–01.htm.

"U.S. Customs Inspectors Seize 3,089 Pounds of Marijuana at World Trade Bridge" [online], May 1, 2001 [retrieved on May 22, 2002], 1 p., Retrieved from the Internet: http://www.customs.gov/hot–new/pressrel/2001/0502–02.htm.

"U.S. Customs Seizes Over a Ton in Off–Road Trailer" [online], Mar. 13, 2001 [retrieved on May 22, 2002], 1 p., Retrieved from the Internet: http://www.customs.gov/hot–new/pressrel/2001/0315–00.htm.

"U.S. Customs Seizes More Than 3,300 Pounds of Marijuana Hidden Inside Cargo Container" [online], Mar. 9, 2001 [retrieved on May 22, 2002], 1 p., Retrieved from the Internet: http://www.customs.gov/hot–new/pressrel/2001/0313–00.htm.

"U.S. Customs Inspectors Seize $1.5 Million in Cocaine, Currency, Methamphetamine and Marijuana This Weekend at Port of Entry" [online], Feb. 12, 2001 [retrieved on May 22, 2002], 1 p., Retrieved from the Internet: http://www.customs.gov/hot–new/pressrel/2001/0213–02.htm.

"U.S. Customs Service Inspectors Seize 4,946 Pounds of Marijuana at El Paso/Ysleta Cargo Facility" [online], Jan. 30, 2001 [retrieved on May 22, 2002], 1 p., Retrieved from the Internet: http://www.customs.gov/hot–new/pressrel/2001/0130–02.htm.

"U.S. Customs Inspectors Seize 2,939 Pounds of Marijuana at World Trade Bridge This Weekend" [online], Jan. 29, 2001 [retrieved on May 22, 2002], 1 p., Retrieved from the Internet: http://www.customs.gov/hot–new/pressrel/2001/0130–01.htm.

"Containing Terror—Electronic Seals and Tracking Efforts Boost Cargo Security," Technology Review, pp. 24–25, Sep., 2003.

Malotky, Lyle O., Pennella, John J., "Physics–Based Technologies for the Detection of Contraband,"SPIE–The International Society for Optical Engineering,vol. 2936, pp. 112–123, Nov. 19–20, 1996.

Verbinski, Victor V., Orphan, Victor J., "Vehicle and Cargo Inspection System,"SPIE, vol. 2867,pp. 235–238.

Orphan, V., Muenchau, E., Gormley, J., Richardson, R., "Advanced Cargo Container Scanning Technology Development," Science Applications International Corporation, San Diego, California.

SAIC: News Release dated Jun. 17, 2004, http:www.saic.com/news/2004/jun/17.html (2pp.).

SAIC: News Release dated Aug. 25, 2004, http://www.saic.com/news/2004/aug/25.html (2pp.).

SAIC: News Release dated Oct. 20, 1999, http://www.saic.com/news/oct99/news10–20–99.html (2pp.).

Innovation Technology Summary Report (DOE/EM–0543), "Waste Crate and Container Imaging Using the Vehicle and Cargo Inspection System," Jul. 2000 (28pp.).

"Smugglers beware, gamma rays on deck," http://nb.cbc.ca/regional/servlet/View?filename=nb_gammaport20030911 (2pp.).

"Major upgrade for port security —Contracts signed for $1 billion X–ray equipment," http:www.portjam.com/major_upgrade_for_port_security.html (2pp.).

Washington Technology, "SAIC Sells Imaging Systems to Customs Service," http:www.washingtontechnology.com/cgi–bin/udt/im.display.printable?client.id=wtdaily–.. (1p.).

Sandifur and Lanaux, Port Technology International, "Wireless and traditional technology to secure Port of Oakland" (3pp.).

Maryland Department of Transportation, "Congressman Cardin Unveils Gamma Ray Scanner at Port of Baltimore," http:www.mdot.state.md.us/News/2003/February2003/MPA%20VACIS (2pp.).

Barber, Seatle Port–Intelligencer, "Port gets a new tool to fight terrorism," http://seattlepl.nwsource.com/printer2/index.asp?ploc=t&refer=http:seattlepi.nwsource.co.. (3pp.).

"Mobile VACIS®Inspection System, Technical Specifications"[online], [retrieved on Jul. 8, 2004], 4 pp., Retrieved from the Internet: http://www.saic.com/products/security/mobile–vacis/mobile–tech.html.

"Pallet VACIS®Inspection System, Technical Specifications"[online], [retrieved on Jul. 8, 2004], 2 pp., Retrieved from the Internet: http://www.saic.com/products/security/pallet–vacis/pallet–tech.html.

"Portal VACIS®Inspection System, Technical Specifications"[online], [retrieved on Jul. 8, 2004], 3 pp., Retrieved from the Internet: http://www.saic.com/products/security/portal–vacis–tech.html.

"Railroad VACIS®Inspection System, Technical Specifications"[online], [retrieved on Jul. 8, 2004], 3 pp., Retrieved from the Internet.

"Relocatable VACIS®Inspection System, Technical Specifications"[Online], [retrieved on Jul. 8, 2004], 3 pp., Retrieved from the Internet: http://www.saic.com/products/security/relocatable–vacis/relocatable–vacis–tech.html.

"VACIS® Inspection Systems Combat Contraband Transport" [online], [retrieved on Jul. 8, 2004], 2 pp., Retrieved from the Internet: http://www.saic.com/cover–archive/transport/VACIS.html.

"SAIC Mobile VACIS® Cargo, Vehicle and Contraband Inspection Unit to be Deployed at Latvian Points of Entry" [online ], Jun. 17, 2004 [retrieved on Jul. 8, 2004], 2 pp., Retrieved from the Internet: http://www.saic.com/news/2004/jun/17.html.

"SAIC Canada Completes Acquisition of Exploranium G. S. Limited" [online], Dec. 23, 2003 [retrieved on Jul. 8, 2004], 2 pp., Retrieved from the Internet: http://www.saic.com/news/2003/dec/23.html.

"SAIC Awarded Strategic Port Automation Contract" [online], Oct. 28, 2003 [retrieved on Jul. 8, 2004], 2 pp., Retrieved from the Internet: http://www.saic.com/news/2003/oct/28.html.

"SAIC's Mobile VACIS to Inspect for Explosives and Contraband at U.S. Borders, U.S. Customs Service Awards Contract for 11 Mobile VACIS Units" [online], Oct. 20, 1999 [retrieved on Jul. 8, 2004], 2 pp., Retrieved from the Internet: http://www.saic.com/news/oct99/news10–20–99.html.

SAIC's VACIS II to Search for Contraband at U.S. Borders, U.S. Customs Services Issues Contracts for 29 VACIS II's [online], Jul. 26, 1999 [retrieved on Jul. 8, 2004], 2 pp., Retrieved from the Internet: http://www.saic.com/news/jul99/news/07–26–99.html.

"Rapiscan TVS™ –Truck Validation System" [online], Copyright 1999–2002 [retrieved on Jul. 1, 2004], 3 pp., Retrieved from the Internet: http://www.rapiscan.com/4100.html.

"Mobile VACIS® Inspection System, Overview" [online], [retrieved on Jun. 3, 2004], 2 pp., Retrieved from the Internet: http://www.saic.com/products/security/mobile–vacis/index.html.

"Pallet VACIS® Inspection System, Overview " [online], [retrieved on Jun. 3, 2004], 2 pp., Retrieved from the Internet: http://www.saic.com/products/security/pallet–vacis/index/index.html.

"Portal VACIS® Inspection System, Overview" [online], [retrieved on Jun. 3, 2004], 2 pp., Retrieved from the Internet: http://www.saic.com/products/security/portal–vacis/index.html.

"Railroad VACIS® Inspection System, Overview" [online], [retrieved on Jun. 2, 2004], 2 pp., Retrieved from the Internet: http://www.saic.com/products/security/rr–vasic/index.html.

"Relocatable VASIC® Inspection System, Overview" [online], [retrieved on Jun. 2, 2004], 2 pp., Retrieved from the Internet: http://www.saic.com/products/security/relocatable–vacis/index.html.

"Rapiscan GaRDS™ –Gamma Radiographic Detection System" [online], Copyright 1999–2002 [retrieved on Apr. 5, 2004], 3 pp., Retrieved from the Internet: http://www.rapiscan.com/4200main.html.

"DigestPlus Selector, My Product List" [online], [retrieved on Jun. 3, 2003], 1 p., Retrieved from the Internet: http://ecatalog.squared.com/fulldetail.cfm?partnumber=DTU223NRB.

"Thomas Compressors and Vacuum Pumps, Rietschle Thomas" [online], Copyright 2001 [retrieved on May 15, 2003], 1 p., Retrieved from the Internet: http://www.thomaspumps.com.

"Thomas Compressors and Vacuum Pumps News: Kings of Custom, Rietschle Thomas, Sales & Distribution" [online], [retrieved on May 15, 2003], Retrieved from the Internet: http://dealer.thomaspumps.com/dealers/list_us_distribs.asp?request=5.

"Double Throw Safety Switches — Fusible and Not Fusible Class 3140, 30 (Series T4), 200–600 A Types 82,000, 92,000 and 200 A DTU (Series E)" [online], [retrieved on Feb. 19, 2003], 1 p., Retrieved from the internet: http://ecatalog.squared.com/catalog/html/sections/03/17203014.htm.

"Double Throw Safety Switches, Fusible and Not Fusible, Class 3140, New — Series F," Copyright 2002, 1 p.

SeaLevel Systems Incorporated, "Ultra 485™ User Manual," Copyright 1999, 24 pp.

Hasegawa, Bruce, H., et al., "A Prototype High–Purity Germanium Detector System with Fast Photon–Counting Circuitry for Medical Imaging," Med. Phys., vol. 18, No. 5, pp. 900–909, Sep./Oct., 1991.

Grainger, "Electrical Distribution Safety Switches, Double Throw, Non–Fusible Switches," 1 p.

Grainger, "Marine Rated Devices," Catalog, p. 331.

Hubbell, "Marine Products, 50 Ampere, 125/250 Volt, 3 Pole 4 Wire, Ship–to–Shore Devices," 1 p.

Hubbell, "Marine Products, Internationally Rated, 16, 32, 63 Ampere, 240 Volt, 50 Cycle, Pine and Sleeve Devices," 1 p.

Rapiscan Cargo Inspection Products, "Rapiscan 4100,"2 pp.

Boyd, Douglas P., Chapter 130, "Transmission Computed Tomography," Future Technologies, pp. 4357–4371.

Thomas Pumps & Compresors, "WOB–L®Piston, Pumps and Compressors, 607/668/669/688/689 Series," 2 pp.

Docket for Rapiscan Security Products, Inc., v. Science Applications International Corporation,.

"Industrial X–Ray Units," Trade Brochure, General Electric X–Ray Corporation, Pub. 7A–700.

Richardson, Rex D., et al., "New Cargo Inspection and Transportation Technology Applications" [online], [retrieved on Feb. 18, 2004], pp. 83–90, Retrieved from the Internet: http://www.saic.com/products/security/relocatable–vacis.

O'Brien, Gregory, et al., "Non–Intrusive Container Inspection" [online], [retrieved on Feb. 18, 2004], pp. 1–3, Retrieved from the Internet: http://www.saic.com/products/security/relocatable–vacis.

Orphan, Victor J., et al., "VACIS® –A Safe, Reliable and Cost–Effective Cargo Inspection Technology" [online], [retrieved on Feb. 18, 2004], pp. 61–65, Retrieved from the Internet: http://www.saic.com/products/security/relocatable–vacis.

Verbinski, Victor, et al., "Recent Developments in the VACIS Gamma Radiography Systems, " Part of the SPIE Conference on Enforcement and Security Technologies, Boston, Massachusetts,SPIE vol. 3575, pp. 368–374, Nov. 1998.

Verbinski, Victor V., "Cargo Vehicle Inspection System," Sep. 28, 1995, Proceedings — Counterdrug Law Enforcement: Applied Technology for Improved Operational Effectiveness International Technology Symposium,Nashua, New Hampshire, Oct. 24–27, 1995, pp. 14–9 –14–28.

"Imaging Gamma–Ray Contraband Detector for Empty Liquid Transport Containers," Quarterly Report, Work Carried Out Under: Contract No. DABT63–94–C–0039 (ONDCP), Prepared for: COTR: John Shaver, U.S. Army Electronic Proving Ground, Report Prepared By: Victor Verbinski, Science Applications International Corporation, 15 pp., Nov. 21, 1994.

Award/Contract No. DABT63–94–C–0039, Issued By: Directorate of Contracting, Contractor: Science Applications International Corporation, Ship to: Office of National Drug Control Policy, Payment Will Be Made By: Defense Finance & Account Svc., Defense Accounting Office, 32 pp., Aug. 1994.

Verbinski, Victor V., "Contraband Detector for Tanker Trucks and Similar Vehicles," Jul. 28, 1993, *Proceedings – Tactical Technologies and Wide Area Surveillance International Symposium*, Chicago, Illinois, Nov. 2–5, 1993, pp. 23–42.

"Proposal to Develop Imaging Gamma–Ray Contraband Detector for Empty Liquid Transport Containers," Technical vol., Submitted to: Excecutive Office of the President, In Response to: ONDCP Broad Agency Announcement (BAA) 92–15 (Log No. 92–15–A222), Submitted By: Science Applications International Corporation, 54 pp., May 6, 1993.

"Contraband Detector For Tanker Trucks: Feasibility Study," Technical Proposal, Submitted to: Department of the Treasury, U.S. Customs Service, Contract No. TC 81–14, Submitted By: V. Verbinski, Science Applications International Corporation, 20 pp., Jul. 8, 1991.

* cited by examiner

Detector Configuration:
3 Vertical Rows, 112 in Each Row

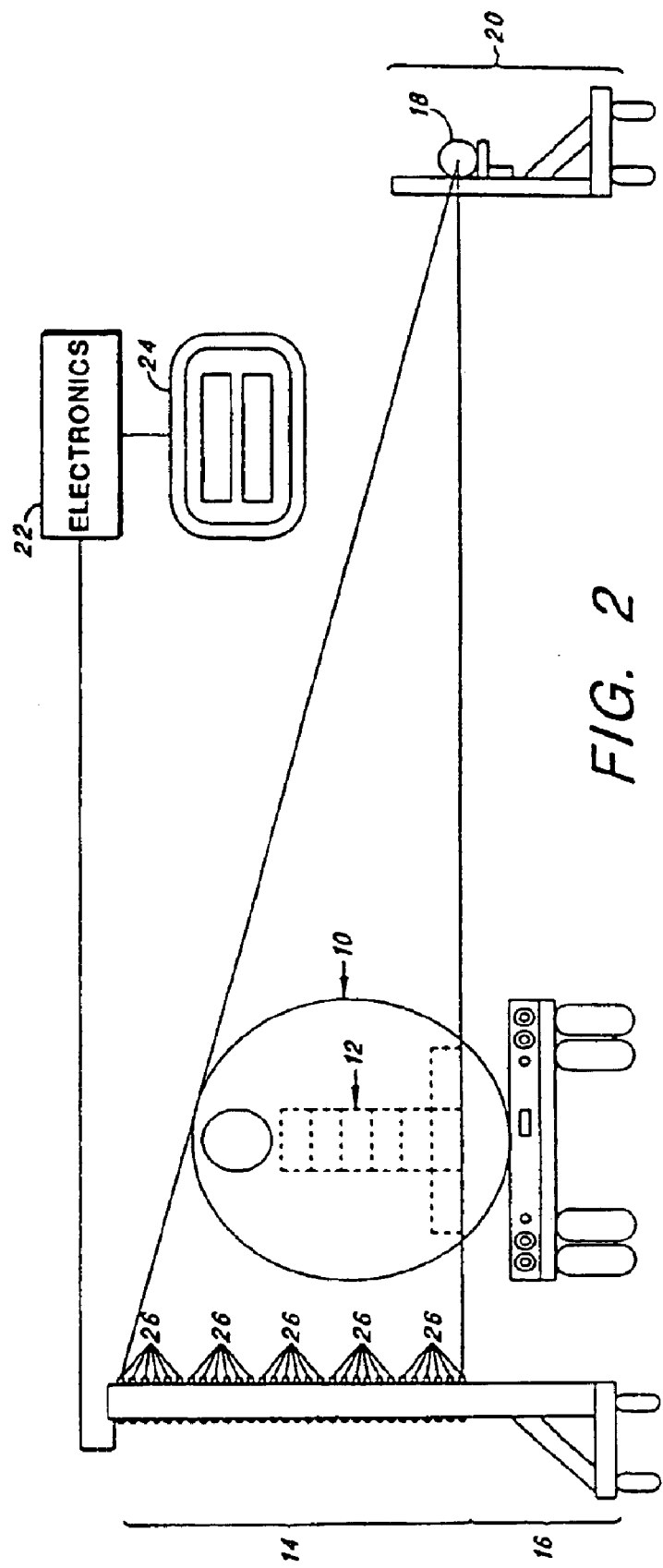

Mobile Vehicle Inspection System

DENSITY DETECTION USING REAL TIME DISCRETE PHOTON COUNTING FOR FAST MOVING TARGETS

This is a Continuation-in-Part Application of U.S. Ser. No. 09/398,547, for DENSITY DETECTION USING REAL TIME DISCRETE PHOTON COUNTING FOR FAST MOVING TARGETS, filed Sep. 17, 1999 now U.S. Pat. No. 6,507,025, by Verbinski, et al., which is a Continuation-in-Part Application of U.S. Ser. No. 08/921,854 of Verbinski et al., for DENSITY DETECTION USING DISCRETE PHOTON COUNTING, filed Sep. 2, 1997 now abandoned, which is a Continuation Application of U.S. Ser. No. 08/546,999 of Verbinski et al., for DENSITY DETECTION USING DISCRETE PHOTON COUNTING filed Oct. 23, 1995, now abandoned, both of which are incorporated herein by reference.

A portion of the disclosure of this patent document contains material that is subject to copyright protection. The copyright owner has no objection to the facsimile reproduction by anyone of this patent document or the patent disclosure, as it appears in the United States Patent and Trademark Office patent files or records, but otherwise reserves all copyright rights whatsoever.

BACKGROUND OF THE INVENTION

The present invention relates to density detection using discrete photon counting, and more particularly to using discrete photon counting to generate an image indicative of the densities in a target object. Even more particularly, the invention relates to using discrete photon counting in ultra high-speed real time detection, and distortion-free image processing for a fast-moving target, under acceleration, and with the lowest possible radiation-field strength.

There are many instances in the security or customs field when it is necessary to examine or inspect in a non-destructive way, the contents of a target object, such as a closed package, box, suitcase, cargo container, automobile semi-trailer, tanker truck, railroad car, e.g., box car or tanker car, or the like. For example, customs departments are routinely charged with the responsibility of inspecting vehicles coming into a country to make sure such packages do not contain drugs or other contraband, or leaving the country with stolen automobiles, drug money, and other illicit contraband. Similarly, drug smugglers frequently carry out their criminal acts by hiding illegal drugs in vehicles such as tanker trucks, and then sending the trucks through a border checkpoint. When security personnel encounter suspicious vehicles or other containers being transported over international boundaries, they must perform a careful time consuming (~½ hour) inspection of such vehicles to ascertain their contents. Similarly, when suspicious trucks or cars enter compounds overseas having U.S. troops or containing embassy offices, they must be inspected for hidden vehicle bombs, poisonous gases, etc.

When suspicious vehicles are discovered, they generally must be examined or inspected on location in what is referred to as a "secondary inspection area." If secondary inspection reveals the presence of contraband (e.g., drugs), then the vehicle may be impounded, the driver arrested, and the contraband disposed of. If, on the other hand, the examination reveals the absence of contraband, then the vehicle may be allowed to proceed in normal manner.

The process used to examine or inspect a suspicious vehicle should be quick, simple, as unintrusive as possible and fast enough so as to not impede the "flow of commerce".

Unfortunately, most common conventional inspection mechanisms require either visual inspection by others and/or scent inspection by dogs.

These conventional inspection methods require that the vehicle stop and wait for the inspection to be completed, which can take a half hour or more. This is both inconvenient and time consuming for both customs officials and the vehicle drivers and occupants, and severely limits the number of vehicles that can be inspected each day. Furthermore, such inspection may put officers at personal risk if a vehicle has been booby-trapped or if the vehicle's driver or other occupants become nervous and decide to attack the customs officer inspecting their vehicle. What is needed, therefore, is a rapid, non-invasive technique for inspecting the contents of a suspicious vehicle without requiring that the vehicle be stopped and manually inspected.

One attempt to satisfy this need involves the use of high levels of radiation to determine the densities of the vehicle and/or the contents of such vehicle. Unfortunately, this approach in the prior art requires that the vehicle be stopped and evacuated prior to inspection, because such high levels of radiation can be physically harmful to the vehicle's occupants if they remain in the vehicle during inspection.

Disadvantageously, prior art inspection systems using high levels of radiation not only require that the vehicle be stopped, and therefore delayed, but pose a risk to stowaways that may be aboard the vehicle, and unwilling to voluntarily evacuate when the vehicle is stopped for inspection. Therefore, what is needed is a non-invasive technique for inspecting the contents of a suspicious vehicle without requiring the use of high levels of radiation. (The embodiments of the invention described herein expose the cargo to only about 5 microroentgen of gamma radiation which is equivalent to about 15 minutes worth of natural background radiation.)

A further problem posed by manual inspection techniques arises when tanker trucks or railroad cars, after having been emptied, seek to cross a border in order to refill. Because some such tankers (e.g., liquified petroleum gas tankers that are of thick, double-walled steel construction) cannot be completely emptied without releasing the pressure in such tankers and venting noxious (and explosive) gasses into the atmosphere, the tankers typically are kept nominally under pressure. (The venting of noxious gasses would be hazardous and ecologically unacceptable.) Thus, the contents of such tankers typically go uninspected by customs agents in order to avoid the time-consuming (up to 3 days, with nitrogen purging) venting of such gases. Unfortunately, drug smugglers are well aware of this fact, and therefore utilize tanker trucks and railroad cars to import illegal drugs, knowing that they will not be inspected at the border. This venting condition provides just one of numerous additional examples of cases where invasive or intrusive inspection into vehicles, or other containers, is not feasible or desirable. Thus, this venting condition further emphasizes the need for a non-intrusive approach to vehicle inspection, especially by a high-energy gamma-ray radiographic system that easily penetrates the steel walled tanker.

Yet a further problem with prior vehicle inspection systems is that some, employing complex x-ray inspection sources, move a vehicle past a source and detector, which constitute heavy equipment subject to frequent breakdowns, and requiring very high capital costs for installation. Some inspect at a rate as low as 10–15 minutes per cargo vehicle, according to U.S. Customs Inspectors.

Additionally, some prior systems employing a high intensity standard X-ray radiation source require, at the beginning of the day, from one-half hour to 1 hour to warm up, depending upon the intervals between use. The X-ray source is expensive to buy and to install and requires an appreciable amount of power to operate, is sensitive to ambient humidity and motion-shock and is expensive and time- consuming to repair.

Furthermore, these expensive X-ray sources also require a permanent shielding structure, which, along with the vehicle-moving mechanism, boosts the capital costs to nearly $10,000,000 for one such system, limiting the numbers which can be in use at borders.

Therefore, there is a widely known need in the industry of cargo-vehicle inspection systems for a mobile vehicle inspection system capable of detecting contraband on the order of a pound (or better) in a large, fast-moving vehicle, with the use of relatively very low intensity radiation (on the order of 1 Curie or less), in a manner which can be done swiftly so as not to hold up vehicle-traffic at border inspection points, and affordably, even with a fast-moving, large, accelerating vehicle, accelerating at an unpredictable rate.

The present invention advantageously addresses the above and other needs.

SUMMARY OF THE INVENTION

The present invention advantageously addresses the needs above as well as other needs by providing a system and method employing discrete photon counting, and a relatively very low intensity radiation source, to perform ultra high-speed real-time density measurements in a fast-moving target object and to generate a distortion-free, high resolution image of contents of such fast-moving (and accelerating), target object in response thereto.

In one embodiment, the invention is characterized as a system that uses discrete photon counting to generate a graphical display indicative of densities in a target object. The system comprises: a radiation source having a variable, controlled position relative to the target object to radiate photons toward the target object; an array of photon detectors having a variable, controlled position relative to the target object to receive photons passing through the target object, wherein the array of photon detectors is surrounded by a radiation shield; a motion controller coupled to the radiation source and the array of photon detectors for determining and controlling motion of one or more of the detector array and the radiation source, such that a constant distance is maintained therebetween; a counter comprising an amplifier, a discriminator, and a pulse generator for each photon detector and means for discretely counting photons received by each photon detector; and a display responsive to the counter for generating a graphic display of densities in the target object.

In another embodiment, the invention is characterized as a system for minimizing scattered radiation from impinging on an array of photon detectors for generating a graphical display indicative of densities in a target object using discrete photon counting. The system comprises: a radiation source having a variable, controlled position relative to the target object to radiate photons toward the target object, wherein the radiation source produces a fan beam and further wherein the radiation source is movable so as to be adjusted to irradiated target objects of varying heights with the fan beam; an array of photon detectors having a variable, controlled position relative to the target object to receive photons passing through the target object, wherein the array of photon detectors is surrounded by a radiation shield; a radiation filter positioned between the target object and the array of photon detectors for blocking unwanted radiation from impinging upon the array of photon detectors; an array of photon collimators, positioned in one-to-one alignment with the array of photon detectors to receive and collimate the photons from the radiation source; and a laser pointer attached to the radiation source for indicating the location of the ground relative to the bottom of the array of photon detectors for aligning the radiation source, whenever it is repositioned, such that the fan beam irradiates the array of photon detectors and not the ground.

In a further embodiment, the invention is characterized as a system using discrete photon counting to generate a graphical display indicative of densities in a target object. The system comprises: means for radiating photons toward the target object; means for receiving photons passing through the target object, wherein the means for receiving photons is surrounded by a means for shielding the means for receiving photons from radiation; means for determining and controlling motion of one or more of the means for receiving photons and the means for radiating photons, such that a constant distance is maintained therebetween; a counter comprising an amplifier, a discriminator, and a pulse generator for each photon detector and means for discretely counting photons received by each photon detector; and means for generating a graphic display of densities in the target object.

In yet another embodiment, the invention is characterized as a linear detector array system for use in a target inspection system for detecting a contents of the target. The linear detector array comprises: a plurality of vertical rows of staggered detectors, each of the plurality of vertical rows being vertically staggered from each other vertical row, such that a pitch between any two closest adjacent staggered detectors is smaller than a diameter of the staggered detectors.

Further to this embodiment, the linear detector array system comprises a center vertical row of staggered detectors and one or more side vertical rows of staggered detectors and a processor comprising an image-generating program, the processor receiving data from each of the one or more side vertical rows and from the center vertical row. The image-generating program of this embodiment further includes adjustment means for determining an adjustment for a horizontal displacement k of the one or more side vertical rows from the center vertical row, wherein the adjustment is used to correlate the data from the side vertical rows with data from the center vertical row so as to form undistorted images for multiple planes within the target.

Still further to this embodiment, the adjustment means further includes computing means for determining an image adjustment distance 1 for multiple planes within the target according to a relationship 1=kZ/D, wherein Z is variable and is a distance between a radiation source and each of the multiple planes within the target, and wherein D is a distance between the radiation source and the linear detector array.

In yet another embodiment, the invention is characterized as a method for processing staggered detection data for use in a target inspection system. The method comprises the steps of: providing a plurality of vertical rows of staggered detectors, each of the plurality of vertical rows being vertically staggered from each other vertical row, such that a pitch between any two closest adjacent staggered detectors is smaller than a diameter of the staggered detectors including: providing a center vertical row of staggered detectors; providing one or more side vertical rows of staggered detectors; providing a processor comprising an image-generating program; receiving data at the processor from each of the one or more side vertical rows and from the center vertical row; determining an adjustment for a horizontal displacement k of the one or more side vertical rows in order to correlate the data from the side vertical rows with data from the center vertical row so as to form undistorted images for multiple planes within the target.

Further to this embodiment, determining an adjustment for a horizontal displacement k further includes determining an image adjustment distance 1 for multiple planes within the target according to a relationship 1=kZ/D, wherein Z is variable and is a distance between a radiation source and each of the multiple planes within the target, and wherein D is a distance between the radiation source and the linear detector array.

Still further to this embodiment, the method comprises adjusting the data from the one or more side vertical rows and the center vertical row using the adjustment distance 1 for each of the multiple planes to form undistorted images for each of the multiple rows and comparing the undistorted images for each of the multiple planes to determine the location of an object within the target.

BRIEF DESCRIPTION OF THE DRAWINGS

The above and other aspects, features and advantages of the present invention will be more apparent from the following more particular description thereof, presented in conjunction with the following drawings wherein:

FIG. 2 is a schematic diagram of a system made in accordance with another embodiment of the present invention and of a tanker truck containing contraband material, wherein discrete photon counting is used to perform density measurements in a tanker truck and wherein an image is generated of the contents of such tanker truck in response thereto;

Figure 4:
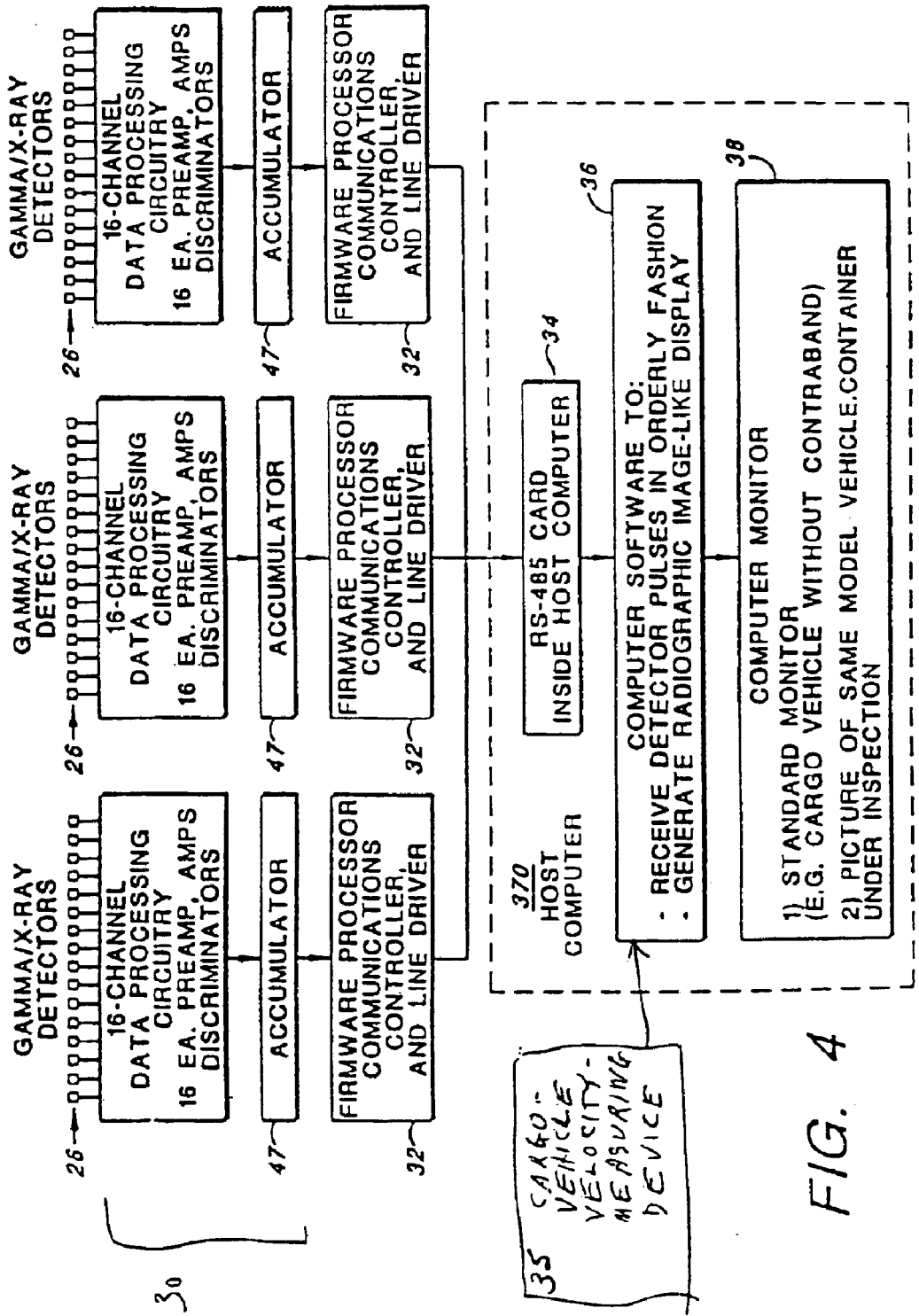
FIG. 4 is a block diagram of the system of FIGS. 1, 2 and 3 showing gamma/x-ray detectors coupled through 16-channel processing units, accumulators, RS-485 line drivers, and an RS-485 interface card to a computer, wherein the computer processes discrete photon count information and target velocity from detectors and a velocity-measuring device and causes a display device to display an image of contents of a fast-moving target object, such as the tanker truck of FIGS. 1 and 2, in response thereto.

APPENDIX A is a source code listing of a firmware operating system including steps traversed by each 16-channel processing unit of FIG. 4 in order to quickly relay the photon count information received from the detectors to the computer.

Corresponding reference characters indicate corresponding components throughout the several views of the drawings.

DETAILED DESCRIPTION OF THE PREFERRED EMBODIMENTS

The following description of the presently contemplated best mode of practicing the invention is not to be taken in a limiting sense, but is made merely for the purpose of describing the general principles of the invention. The scope of the invention should be determined with reference to the claims.

Figure 1:
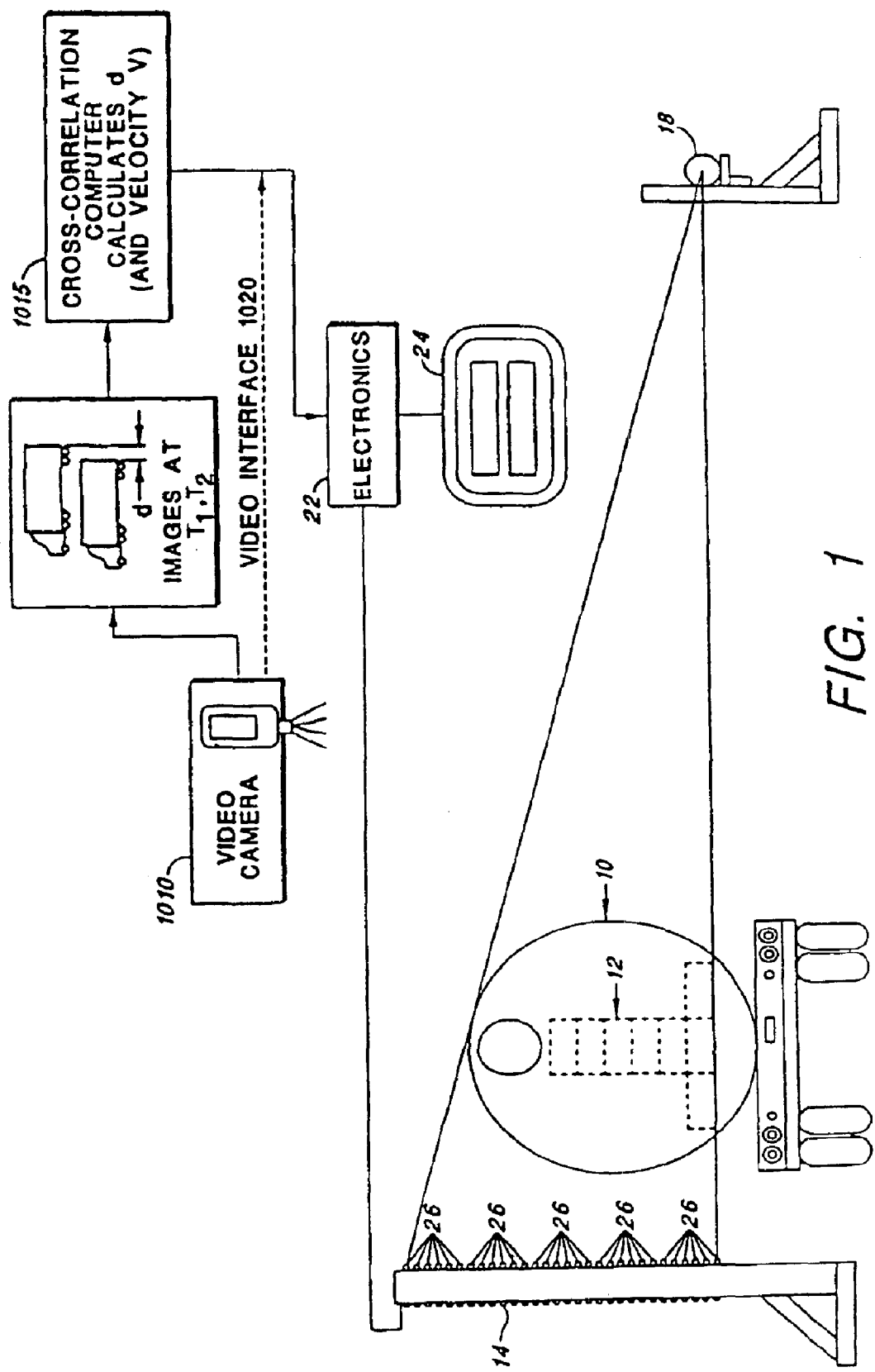
FIG. 1 is a schematic diagram of a system made in accordance with one embodiment of the present invention and of a tanker truck containing contraband material, wherein discrete photon counting is used to perform density measurements on a tanker truck in conjunction with cross correlation means for velocity measuring, wherein a velocity-compensated image is generated of the contents of such tanker truck in response thereto.

Referring first to FIG. 1, a schematic diagram is shown of a system made in accordance with one embodiment of the present invention and of a fast-moving target object 10 ("target object", or "tanker truck", "truck", or "railroad car") containing contraband, wherein discrete photon counting is used with one of several possible velocity-measuring means, a cross-correlation velocity measuring means, to measure density, an image is generated of measured density in response thereto.

Shown in FIG. 1 are the fast-moving target object 10, concealed contraband 12, a detector array 14, a radiation source 18, electronics (or "computer electronics")22, a graphical display device (display) 24, a video camera 1010, a video interface 1020, and a cross-correlation computer 1015.

In an alternative configuration illustrated in FIG. 2, and described later herein, the radiation source 18 and the detector array 14 are uniformly able to move with respect to the stationary target object 10.

By comparison, in the configuration of FIG. 1, the fast-moving target object 10 (or truck or railroad car) being inspected can be driven between the detector array 14 and the radiation source 18 at highway speeds of up to about 60 miles per hour or more. In the illustrated embodiment of FIG. 1, the detector array 14 and the radiation source 18 are both stationarily mounted.

The detector array 14 employs a plurality of "oversized" high efficiency gamma-ray detectors 26, e.g., up to three hundred and thirty-six (336), detectors arranged in a vertical column. The detectors 26 make it possible to scan the fast-moving target object (tanker truck or railroad car) 10 with a very low intensity gamma-ray field. In order to facilitate the use of very low intensity gamma-radiation, the oversized detectors 26 are used, such as are available as Part No. 1.5M1.5M1.5, NaI (T1) (sodium iodide crystal, thallium activated) (with R2060 photomultiplier tube) from BICRON of Ohio. Such gamma-ray detectors are scintillation counter-type detectors and are 1.5" in diameter, 2.5" high, and mounted on a 1.5" photo-multiplier tube (PMT).

Further, in an alternative embodiment of the present invention, each of the detectors is equipped with a radiation collimator in the path of the incoming source radiation. Also to reduce the unwanted background of gamma-rays scattered by the target, e.g., truck, and by the ground, i.e., when the impinging fan beam strikes the ground, the detector array is surrounded by, for example, lead shielding. This shielding and collimation improves the image crispness and depth of radiation penetration. The lead shielding or similar shielding may surround the entire detector array or alternatively, may be place around the individual detectors within the detector array.

Optionally, an analogous detector of around 0.5 to 1.5" in diameter may be used to obtain a finer grid unit mapping of 0.4 to 1.0 inches along one or more dimensions of the fast-moving target object 10.

Alternatively, detectors having a pitch P (i.e., space from one detector center to a next closest detector center) of 0.4 to 1.0" are used to scan a smaller grid unit along the fast-moving target object 10 to a pixel, using a similar configuration of the target object 10, the radiation source 18 and the detector array 14.

Optionally, a pitch P of smaller than twice a radius of the detectors 26 is achieved by staggering detectors vertically such that their circular surfaces lie in a single plane, thereby avoiding any shadowing of detectors by other detectors, and then compensating for the staggering by computer computations as described in detail later herein.

The very low intensity gamma-ray field useable with gamma-ray detectors 26 is low enough in intensity to allow operating personnel to work within it, when a fast opening shutter ("shutter"; not shown) of the radiation source 18 is closed. In the illustrated embodiment the shutter is opened only when an image is being generated, preferably after all personnel leave an area swept out by a fan beam of the radiation source 18.

For example, the very low intensity gamma-ray field may use 662 keV gamma-ray energy from a Cs-137 radiation source. However, a stronger gamma-ray or x-ray source than this can be used, in the interest of faster density measurements, while still allowing operating personnel to safely work within the very low intensity field. The 662 KeV gamma-ray energy can be used, however, when the vehicle under inspection is traveling at high-speeds e.g., railroad freight car or highway speeds, and when the shutter is opened, e.g., after a truck driver or train engineer has passed.

Preferably the radiation source 18 is, in one configuration, a 1, 1.6 or 2.0 Curie shuttered monoenergetic source of Cs-137 gamma-rays (662 keV gamma-ray energy).

Alternatively, a nearly mono-energetic Co-60 source may be used which emits photons at 2 energy levels, in particular, 1170 and 1339 keV. A monoenergetic or near mono-energetic source is preferable, however, because energy-level filtering of the "softer component" (as in X-rays) can be eliminated. A suitable source is readily available as Model No. SH-F2 from Ohmart Corporation of Ohio. The radiation source is used in combination with a collimator that provides a 60° vertical opening (measured from horizontal upwards) and a 10° lateral opening resulting in a narrow, vertical fan beam, utilizing a post-collimator that makes the beam just barely wide enough to irradiate the vertical detector stack. The fast-opening shutter is electrically actuated.

The radiation source 18 provides gamma-rays that are of high enough energy levels (e.g., 662 KeV) to be penetrating of steel walls and only moderately attenuated by steel walls typically found in tanker trucks or railroad cars. Yet such rays are sufficiently attenuated by contraband packages to make them easily detectable by measuring the penetration of the gamma-rays emitted from the source and deriving relative material densities therefrom. In addition, there is negligible backscattering of the gamma-ray energy from the tanker walls, and, in any case, much less than would occur if a high-powered x-ray source was utilized. (Although, a highly filtered x-ray source could, in other embodiments, be employed for high-speed inspection applications or for inspection of unmanned vehicles, such a highly filtered source adds costs and complexity to the system, and detracts from reliability. For these reasons, it is not preferred.)

In an embodiment of the present invention, the narrow fan beam is adjustable, so as to cover different cargo heights and distances from the detector array, while maintaining full irradiation of the detector array. Consequently, in this embodiment, the radiation source is mounted so as to be movable. Further, in order to maintain full irradiation of the lowest detector without irradiating the ground and causing excessive back scatter a laser-beam pointer, used to align the movable radiation source, is adjusted so as to point just a few inches below the lowest detector. In this way, ground-scattering background is greatly reduced, resulting in improved image crispness and depth of penetration.

Referring still to FIG. 1, a velocity measuring system using a cross-correlation method, employs the video camera 1010 coupled to the cross-correlation computer 1015 through the video interface 1020, to measure a velocity v of the fast-moving target object 10 at the cross-correlation computer 1015, using photographic images taken at times $T_1$ and $T_2$, by the video camera 1010. The cross-correlation computer 1015 sends velocity information to the electronics 22 (including a computer). The video camera 1010, located a distance D from the fast-moving target object 10 (e.g., a tanker truck), takes a first photographic image (a "frame" or "first image") at $T_1$: it then takes a second photographic image ("second image") at $T_2$. Times $T_1$ and $T_2$ correspond to a difference in time $\Delta T$. The fast-moving target object 10 moves a distance $\Delta d$ in the time $\Delta T$. The Computer 1015 calculates a ratio $$\frac{(\Delta d)}{(\Delta T)}$$

equal to a velocity, v, of the fast-moving target object 10 and utilizes the varying value of v to determine a count time per grid unit (or "mapped pixel unit" or "mapped pixel size") at time $T_1$ through $T_2$ to produce an undistorted image (i.e., where a square is not imaged as a shortened or lengthened rectangle).

To obtain $\Delta d$ the second image at $T_2$ is moved until it overlaps with the first image at $T_1$. The distance moved, $\Delta d$, to obtain a best overlap, is rapidly calculated by performing a Fast Fourier analysis on each of the first and the second image in digital format before and after achieving a best overlap. A resulting cross-correlation function yields the distance Δd the fast-moving target object 10 moved between time $T_1$ and $T_2$. The values of Δd and Δt then determine the velocity, of the fast-moving target object 10 during a time span between $T_1$ and $T_2$. The velocity, v, is effectively an average velocity during the time span.

A count time (also "count" or "sample time")$T_c$ at each of the detectors 26 is selected as a function of a fixed distance Δx of travel of the fast-moving target object 10, and of the measured velocity, v, of the fast moving target object 10.

Preferably, to avoid distortion, a value of the fixed distance Δx is the fixed distance horizontal grid unit size and is selected, for example, to be equal to Δy, a vertical grid unit size, wherein Δy is selected according to center to center detector spacing, Pitch, P, wherein Δy=Z/D P, Z=source-target distance, and D=source-detector distance. By setting the value of the fixed distance Δx equal to the vertical grid unit size Δy, an undistorted gamma-ray radiography-like image results, regardless of the velocity of the fast-moving target object 10.

A distortion-free image is generated with pixels (not shown) on the display 24, representing an area of Δx by Δy within the fast-moving target object 10 in real time, line by vertical line, as the fast-moving target object 10 passes between the detector array 14 and the radiation source 18. While the fast-moving target object 10 is in motion, the velocity of the fast-moving target object 10 is either assumed to be constant, or is measured continuously, in which case the count time $T_c$ varies as frequently as each vertical line of pixels. In the later case, the velocity at each instant, is read into the image-generating computer 36 to adjust the count time $T_c$, to the fixed distance Δx, corresponding to the horizontal measure of each horizontal grid unit, ("picture element", or "mapped pixel") during each sample time $T_c$.

Since each grid unit correlated to a pixel, the value of Δx is set equal to Δy, and Δy is proportional to a spacing between neighboring detectors 26, a radiographic-like image in real time, vertical line by vertical line, during relative motion between the fast-moving target object 10, the source 18 and the detector array 14, is achieved without distortion, despite variations in the velocity and acceleration of the fast-moving target object 10 as it passes between the detector array 14 and the radiation source 18.

This image is generated in real-time at high velocities by fast data-processing circuitry 30; drivers 32 and interface 34. For each detector 26, a count rate (or "count") per detector 26 is measured representative of a number of photons passing through the grid unit hitting the detector 26 wherein the count rate is high enough to achieve a statistically accurate measure of a contents or density being sampled in a given grid unit (Δx by Δy), as the fast-moving target object 10 moves a distance Δx at high-speed. The count rate gives a measure of the density or contents of the fast-moving target object 10, by means of the relationship ln (or natural logarithm) $(N_o/N)=(dls)$, where $N_o$ is a detector count rate in air (calibration constant), N is a count rate for a pixel corresponding to a target material of density d, a thickness 1, and a cross-section s, with gamma rays passing through a target area (Δx by Δy).

The count rate is further achieved by a fast analog pulse amplifier 42, (described later herein) as electrically coupled to a photomultiplier-tube type of detector 26 with NaI scintillator, that can operate at a rate of up to two (2) million counts per second. A highspeed discriminator 44, (described later herein) also operational at the count rate, biased above electronic noise, generates a pulse for each gamma ray detected. The pulses are then counted in an accumulator circuit, 47, accessed each count time $T_c$, (wherein $T_c$ equals Δx/v).

For example, with 64 detectors 26 paced at a pitch P of 2.5 inches apart, 36 feet from the radiation source 18 (D=36 feet) and the fast-moving target object 10 at 25 feet from the radiation source 18 (Z=25) then Δy equals $$2.5(25)/36 = \frac{PZ}{D}$$

equals 1.76 inches. Thus, for this configuration, the fixed distance Δx is 1.76 inches. For the fast-moving target object 10 traveling at about 60 miles/hour (966 kilometers/hour), this results in a sample time $T_c$ of about 1.7 milliseconds, meaning that the detectors 26 are sampled, at a frequency of about 600 times per second.

Thus, the vertical "linear array" configuration of the detectors 26 is made to provide a resolution of grid points spaced about every 1.76 inches along the length of the target vehicle, and about 1.76 inches, on average, along the height of the target vehicle (as projected on the target vehicle vertical lengthwise center plane) when the vehicle is close to a detector tower.

This resolution is adequate to achieve a detectability limit of as little as about one pound of contraband per 1.76 inches by 1.76 inches gridpoint (or mapped pixel unit). (It is employed in the STAR (Stolen Automobile Recovery) inspection system for inspection of sealed containers leaving U.S.A.)

By definition, vertical grid unit or vertical scanning length along the target object ("vertical grid unit" or "vertical resolution")Δy is equal to Z/D ·P; (as employed above) wherein Z=the distance from the radiation source 18 to a center of the fast-moving target object 10; D=distance from the detector array 14 to the radiation source 18; and P, pitch=vertical distance from a center of a detector 26 to another center of a next closest detector 26.

In accordance with one variation, the grid unit size corresponding to a pixel can easily be varied by appropriately selecting the location of the vehicle with respect to the radiation source and the detectors 26 within the detector array 14, and by varying the distance between inspection points, Δx, longitudinally via choice of sampling period along the length of the target vehicle. For example, in the above example employing a 2.5 inch pitch, if a vehicle is half way between the radiation source 18 and the detector array 14, the vertical resolution is $2.5/2=1.25$ inches, and the value of Δx is set to 1.25 inches as well.

Spacing between the detectors in the detector array can be varied, or for example, counts from adjacent pairs of detectors in the detector array can be combined, to change the mapped pixel size Δy in the vertical direction.

A smaller grid unit of 0.4 inches or less may be scanned to a pixel by using a pitch, P, or 0.4 to 1.0 inches while holding the value of Z/D from between 1 and 0.4. For example, in an embodiment illustrated by FIG. 1A, three (3) rows of staggered detectors are employed to achieve a pitch smaller than a diameter of the staggered photon detectors 202. A computer corrects for horizontal displacements of two "outside" rows of the three rows of staggered detectors.

Figure 1A:
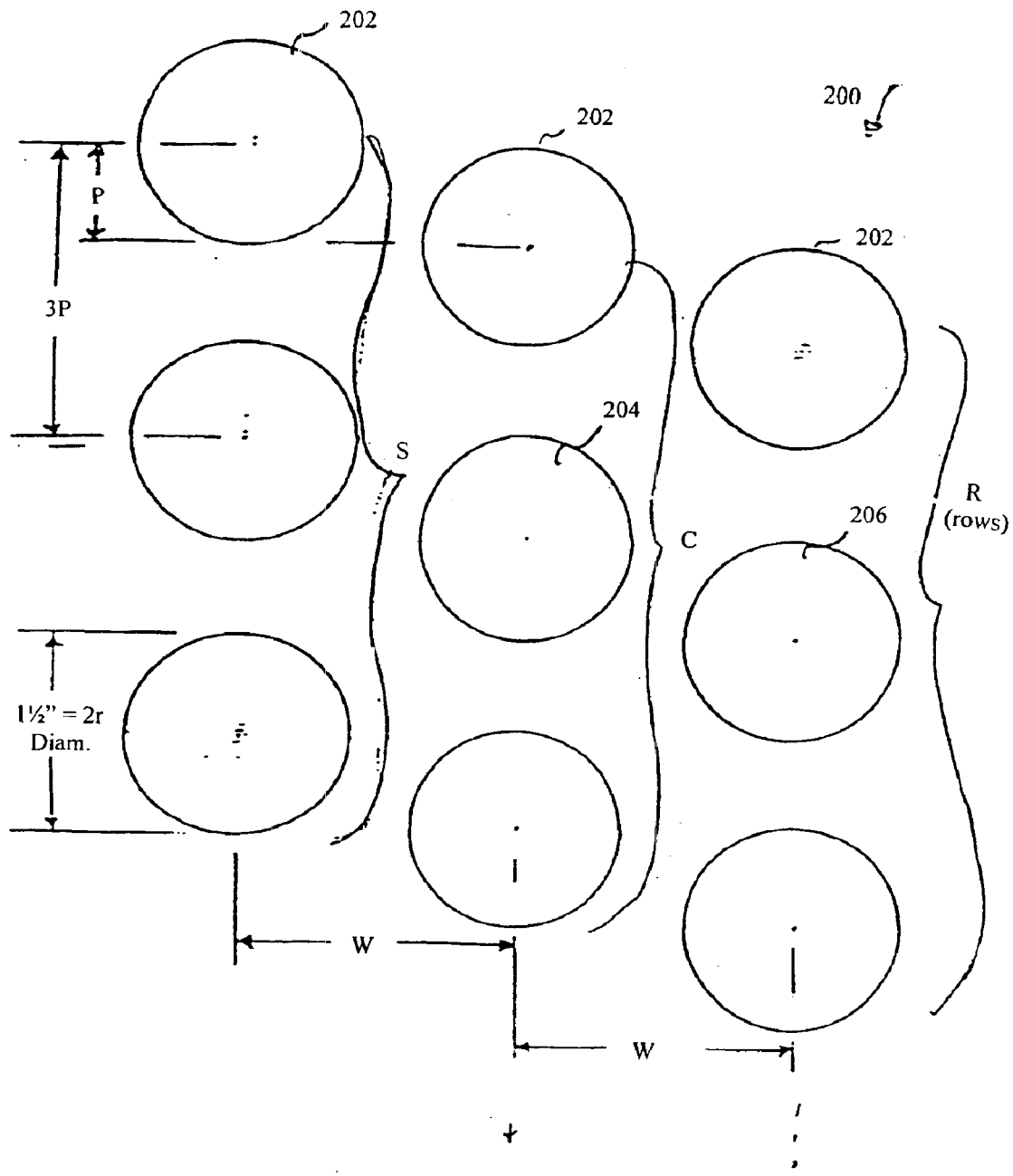
FIG. 1A is an alternate detector configuration to a single row configuration using three vertical rows of staggered detectors to achieve a smaller pitch than would otherwise be possible in a vertical linear detector, for the same detector size (and count rate) and which may optionally be employed in the system of FIG. 1 for an increased image resolution.

Referring next to FIG. 1A, a plurality of staggered photon detectors 202 is employed wherein a low level intensity radiation source (e.g. 1.6 Curies) may optionally be employed in accordance herewith. The staggered detectors

202 may preferably be oversized (e.g. about 1.5" diameter and about 2.5" long) and have a pitch P smaller than the diameter 2r of the staggered detectors 202.

Three (3) vertical rows R of staggered detectors 202 are employed, instead of a single row of detectors 26 shown in FIG. 1. The three (3) vertical rows R are vertically staggered from each other. The pitch P between two (2) closest adjacent such staggered detectors 204, 206 may preferably be about 0.7", when employing staggered detectors 202 having a 1.5" diameter, thereby yielding a count rate of about 20,000 counts/second for each staggered detector 202 for D=35 feet and for a 1.0 Curie Cs-137 source. This pitch P results in a vertical resolution, R, or vertical grid unit of about 0.4", when the radiation source 18 is a distance D of 20' from the staggered detector 202 and the radiation source 18 is a distance z of 11½' from a center of the fast-moving target object 10 wherein $R_{vert}$=PZ/D.

The staggered detectors 202 are staggered from each other in a vertical direction, yet their circular surfaces of each vertical row all lie in a same plane, thereby avoiding shadowing from any other staggered detector 202 while enabling a smaller pitch P.

The image-generating program corrects for horizontal displacement of each of two (2) side rows S 21 the staggered detectors 202 from a center row C (of the 3 vertical rows R) of staggered detectors 202 in the following manner. Further, in an alternative embodiment of the present invention, each of the detectors is equipped with a radiation collimator in the path of the incoming source radiation. Also to reduce the unwanted background of gamma-rays scattered by the target, e.g., truck, and by the ground, i.e., when the impinging fan beam strikes the ground, the detector array is surrounded by, for example, lead shielding. This shielding and collimation improves the image crispness and depth of radiation penetration. The lead shielding or similar shielding may surround the entire detector array or alternatively, may be place around the individual detectors within the detector array.

A center vertical-line image is first generated for the center vertical row C. The image-generating software then superposes on the center row vertical line image, other side images corresponding to each of the two (2) side vertical rows S by moving each of the two (2) side images a distance 1=kZ/D (referred to the center of the fast-moving target 10) in a horizontal direction to coincide with the central-row image, wherein k is a horizon distance between each of the vertical rows R of the staggered detectors 202, and Z and D have been previously defined as, respectively, the distance between the radiation source 18 and the center of the fast-moving target object 10 and the distance between the radiation source 18 and the staggered detectors 202.

For example, employing two (2) vertical rows R of the staggered detectors 202, each of 2¼" diameter, as in the railroad inspection system at Laredo, Tex., the following advantageous results are achievable: (1) the vertical resolution, $R_{vert}$ (vertical grid unit) size is selected to be around 1.0" utilizing staggered detectors 202 with a diameter of 2¼", and (2) the count rate of the staggered detectors may optionally be about 90,000 photon counts/second with the 1.0" vertical resolution, which is high enough to achieve a relatively high speed photon imaging capability for the 1.0" vertical resolution. This count rate is adequate for high speed scanning, yielding about 1000 counts per grid unit at 5 miles per hour and 500 counts per grid unit (pixel) at 10 miles per hour scanning speed.

In this embodiment, the correction, eg., for the sawtooth effect resulting from the use of multiple, staggered rows of detectors, i.e., the rows on either side of the center row, is limited to the select plane located at the center of the target object as defined by distance Z. In an alternative embodiment, image-enhancement software is utilized to facilitate removal of the sawtooth effect for target objects in any plane by, in effect, varying the select plane from the center of the target object Z to the plane z where the actual object of interest (e.g., contraband) is located. The image-enhancement software utilizes least structures image processing. In this process, the depth of the new plane of reference, called z, is recorded and is read out when the operator zooms in on an object of interest. This information reveals the precise (x, y, z) location of the object of interest within the target object. Utilizing this information, the data shifting procedure describe above may be practiced on multiple planes, resulting in the location and a more accurate image of the actual object of interest. A practical application for this image enhancement process is, for example, facilitating the disarming of a truck bomb through the location of the triggering mechanism.

In general, a scanning speed is proportional to a square of a grid unit size. For example, if a 1" grid unit size is increased to a 2" grid unit size, employing the same number of counts/pixel, the scanning speed may be increased by a factor of four (4), since the scanning speed is increased by the square of a ratio of the grid unit sizes (i.e. 2"/1").

Preferably, an entire length of the fast-moving target 10 is scanned automatically with a fan beam, in a single sweep. For example, an entire train of about 100 to 200 freight cars, traveling at up to 10 mph, can be inspected at Laredo, Tex., as the train enters the United States. At these inspection speeds, the "flow of commerce" is not impeded.

Referring next to FIG. 2, an analogous configuration is used for an alternate arrangement employing a radiation source 18 and a detector array 14, wherein the radiation source 18 and the detector array 14 are moving synchronously in respect to a stationary target object 10. Shown in FIG. 2 are the stationary target object (truck) 10, concealed contraband 12, a detector array 14, a detector array truck or trolley 16, a radiation source 18, a radiation source truck or trolley 20, processing electronics 22, a graphical display device 24, and a computer 36.

In this embodiment, the detector array truck 16 and the radiation source truck 20 are designed to travel synchronously along parallel tracks. The trucks 16, 20, are mounted on tracks, and employ a synchronous drive motor (not shown) and a variable frequency generator (not shown) for controlling the speed of the synchronous drive motor, such as are available as Model No. SA0100 from Becker Equipment (Mark Becker P. E.) of Vista, Calif. However, numerous known substitutes can be employed therefore.

In operation, the trucks 16, 20 are moved synchronously along parallel paths spanning the entire length of the target object 10 to be inspected.

In FIG. 2 automatic scanning in the truck-mounted embodiment shown is accomplished when the detector array truck 16 and the radiation source truck 20 move in a parallel fashion along the tracks at a constant speed, with a counting interval selected to effect a longitudinal grid unit size (i.e., grid-spacing interval) of 0.4 to 1 or 1 to 2 inches for a typical tanker truck inspection.

This grid unit size, as mentioned above, can easily be selected by one skilled in the art based on the disclosure provided herein and dependent upon an optimum tradeoff between minimum contraband content detectability, throughput (i.e., inspection time per tanker truck), and gamma-ray field-strength (and other safety concerns).

Thus, in the preferred embodiments shown in FIG. 1, 1A, and FIG. 2, a truly non-invasive inspection technique is provided in which there is no need to manually inspect the vehicle, or, with the fast-opening shutter, to even stop or slow the truck 10. The shutter is opened rapidly after the train engineer's cab, for example, has passed by and is closed after the target object 10 (truck or entire train) passes by. With such rapid inspection capability, the flow of commerce is relatively unimpeded, even with 100% inspection of cargo vehicles.

Figure 3:
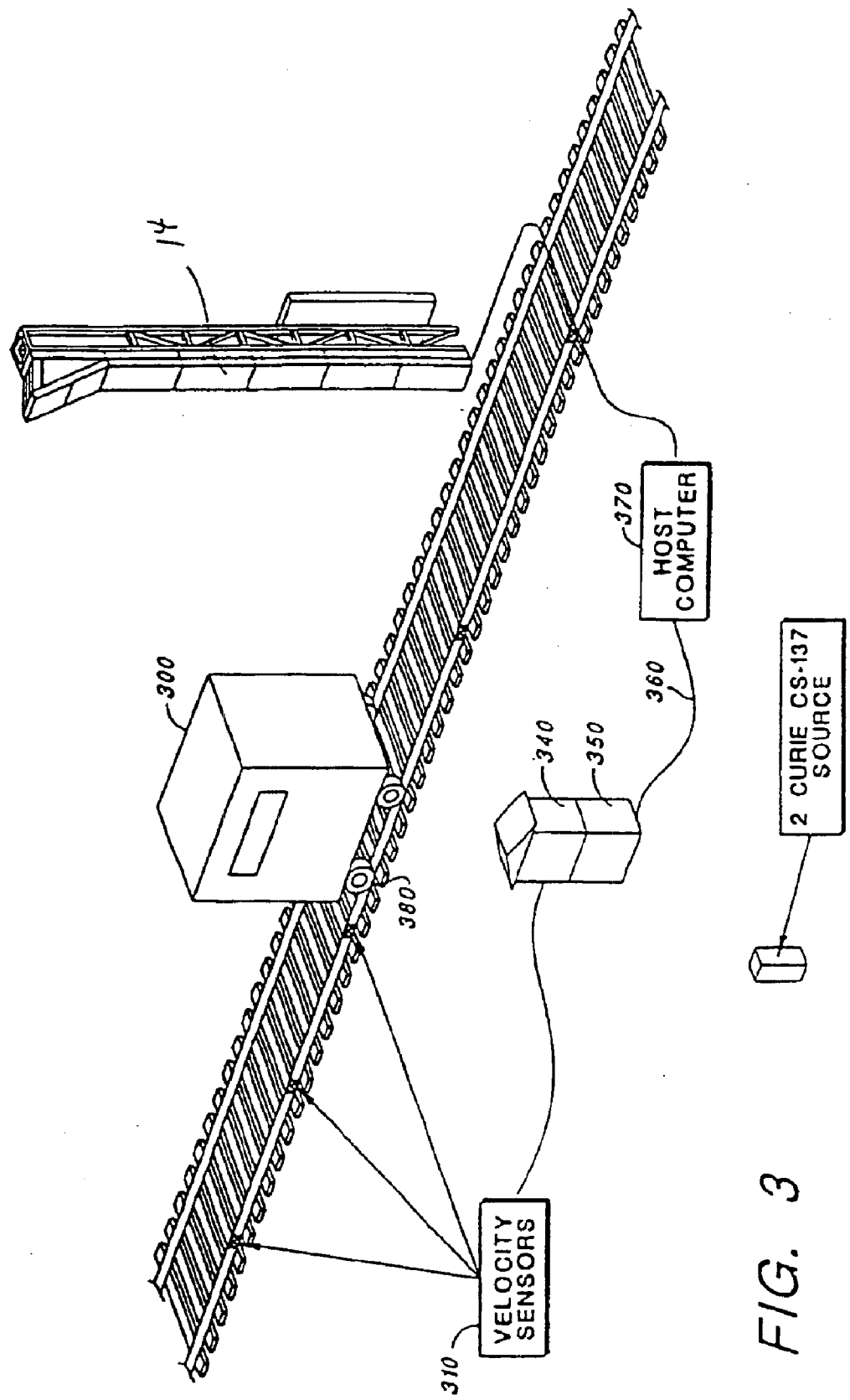
FIG. 3 is a schematic diagram of a system, for inspecting a long train of freight cars, made in accordance with yet another embodiment of the present invention including a magnetic pick-off system (wheel transducer unit) for measuring velocity of a fast-moving target (freight car)

Referring next to FIG. 3, one embodiment of a system made in accordance with yet another embodiment of the present invention including a velocity-measuring system is shown. A similar velocity-measuring system could be employed in the system of FIG. 1 in lieu of the system shown in FIG. 1.

In the case of a train crossing an international border, wherein such train cannot be adequately velocity-controlled for obtaining distortion free images, a velocity-measuring system is extremely advantageous.

In the system shown in FIG. 3, which is especially well suited for railway train applications, a magnetic pick-off system can be employed. The magnetic pick off system illustrated in FIG. 3 includes a pair of velocity sensors (or wheel transducer units) 310, spaced a known distance apart to determine the velocity v of the train 300 at each instant after detecting the train's passage. As a wheel 380 of the train 300 passes each of the pair of wheel transducer units 310, a time is clocked and recorded. A known distance (e.g., inches) and a difference in time is enough to compute the velocity of the train 300. The measured velocity v is calculated by an Auxiliary Processor Unit, 340, coupled to a modem 350. The modem 350 sends a velocity signal through an RS-232 line 360 into a host computer 370 coupled to the RS-232 line 360.

Image software contained within the host computer 370 is then used to compute a detector sampling period or the count time T, so that a contents of the train 300 corresponding to a fixed grid unit size $\Delta x$ and $\Delta y$ defined earlier herein is detected by the detector array 14 and mapped to a pixel in an undistorted fashion. In this fashion, an undistorted image is achieved independent of the velocity v of the train 300 passing between the detector array 14 and the radiation source 18 during each sampling period $T_c$.

Another velocity-measuring system, a doppler radar system (not shown) such as the Railroad Falcon, developed for Science Applications International Corporation (SAIC), of San Diego, Calif. by the FALCON Corporation, measures velocities from 0.3 miles per hour to 99 miles per hour with a precision of ±0.1 miles per hour. This is an alternative method of measuring the velocity v of the truck or the train 300 being inspected. The doppler radar system is similar to a police-type radar gun used for interdiction of speeders along the highway, except it is specially engineered to yield high precision, and to measure down to the very low-velocity limit of trains crossing the border or trucks accelerating from a stand-still. The Railroad Falcon has an RS-232 output for reading the velocity signal into the computer 1015 for generating an image.

Figure 3A:
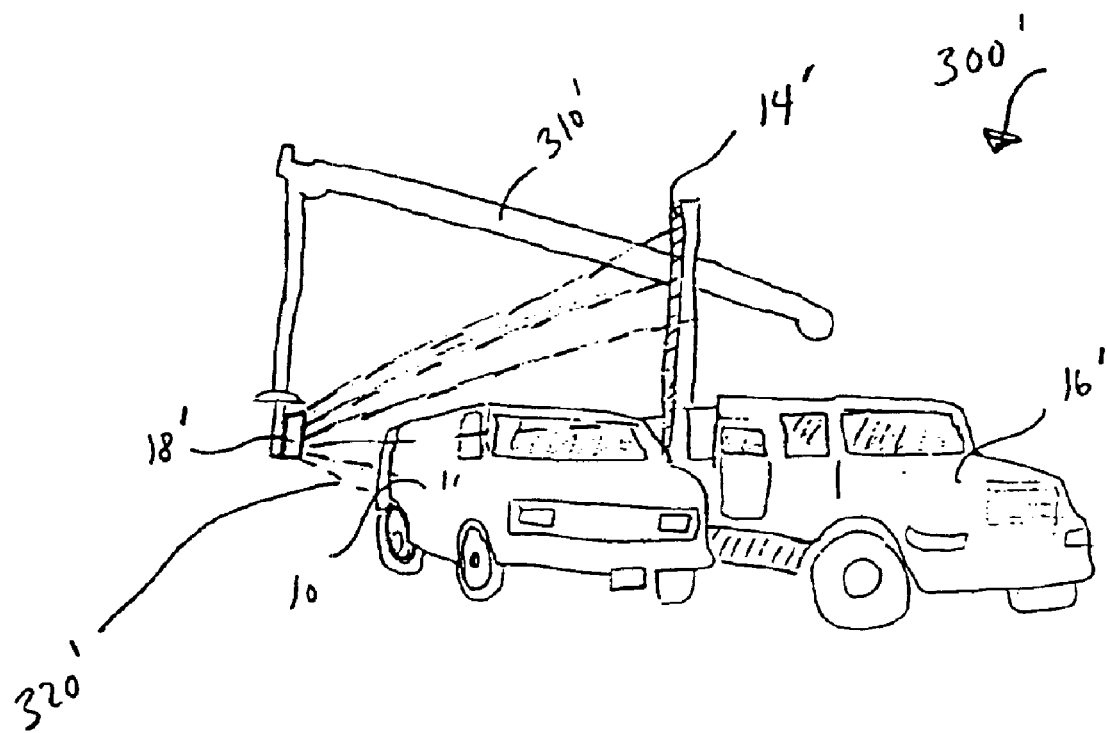
FIG. 3A is a perspective view of a mobile uniplatformed vehicle inspection system employing the detector configuration of FIG. 1A in accordance with a further embodiment of the present invention.

A radar range finder (not shown) with high precision and providing many range readings per second, may also be employed in a further variation of the system, such as a mobile vehicle inspection system such as illustrated in FIG. 3A.

In yet a further variation of the invention system particularly suited for trucks entering an inspection station, the velocity-measuring device may be a commercially available device that utilizes a pressure pad that is activated when a truck tire passes over the pressure pad. Employing two or more such pressure pads, spaced at a known distance apart, provides a measure of the velocity of the vehicle that can be fed to the processing electronics 22 (FIGS. 1 and 2) as a part of the image generation process.

However, regardless of how the velocity information is generated and regardless of the particular embodiment of the system employed, the velocity information is fed into the processing electronics 22 (FIGS. 1 and 2) to determine the sampling period or count time T for the detectors 26, so as to obtain a fixed horizontal grid unit size, $\Delta x$, that matches the vertical grid unit size, $\Delta y$ determined by the pitch, the vertical spacing between detectors, and the proximity of the train 300 or the fast-moving target 10 to the radiation source.

Thus, employing any of the variations of the velocity-measuring system, if a sufficiently high field-strength (or field intensity) is utilized, the detector 26 array 14 (FIGS. 1 and 2) and the radiation source 18 may be fixed or stationary rather than mounted on the radiation source truck (or trolley) 20 and the detector array truck (or trolley) 16 illustrated in FIG. 2. In such an arrangement, the tanker truck 10 or railroad car can be driven past the detector array 14 and radiation source 18 with the determination as to the densities within the truck 10 being made automatically by adjusting the time interval of detector readings in order to normalize the horizontal pixel width $\Delta x$ as the truck 10 or railroad car passes between the radiation source 14 and the detector array 18.

In a variation of the above-embodiment, the fast-opening shutter ("shutter" not shown) adds further protection of an occupant of the fast-moving target object 10, the train 300 or the truck 10 of FIG. 2. In accordance with this variation of the invention, the shutter, placed at the radiation source 18, in a line-of-sight to the detector array 14, remains closed when an occupant passes through the line-of-sight. When closed, the shutter blocks gamma rays from leaving the radiation source 18, providing heightened safety by not exposing the occupant to the radiation.

The shutter opens very quickly (e.g., in 250 milliseconds) after an engine passes the radiation source 18, if the engine is in front of the fast-moving target object 10, the train 300 or truck 10. The shutter closes before the engine passes the radiation source 18, if the engine is in back of the fast-moving target object 10. For added safety, this shutter closes by return-spring action in event of an electrical power failure.

Referring next to FIG. 3A, a mobile, uniplatformed, vehicle inspection system (mobile system) 300' is shown wherein both a radiation source 18' and a linear detector array 14' are mounted on only one mobile platform, such as a truck, and are deployed using a controllable source boom (source boom) 310' to effect the proper spacing for passage of a fast-moving or stationary target 10 therebetween.

The mobile system ("mobile system") 300' comprises a truck 16'; the radiation source 18' suspended at the end of the controllable source boom 310' that is coupled to the truck 16'; and the linear detector array 14' also coupled to the truck 16'. The source boom 310' is long enough such that when it is deployed, the radiation source 18' and the linear detector array 14', are sufficiently laterally spaced so as to allow for the passage of the fast-moving target 10 therethrough.

The mobile system 300' is optionally used in two possible modes of operation, 1) a stationary-target mode, and 2) a fast-moving (or moving) target mode. The radiation source 18', such as a 1.6 Ci Cs-137 source, is suspended from a far end of the source boom 310' so as to facilitate imaging of the fast-moving target object 10 in either of the two possible modes. The radiation source 18' is opened during scanning of the fast-moving target object 10, and a narrow fan-shaped beam is directed at the linear detector 14'.

In one configuration, the linear detector 14' is a 15' high detector array including five (5) three foot modules. Each three-foot module comprises three (3) vertical rows of 1.5 inch diameter, 2.5 inch long NaI (TI) detectors, with sixteen (16) detectors 26 in each vertical row. The three (3) rows are staggered vertically, such as illustrated by FIG. 1A, such that the staggered detectors 202 of 1.5 inch diameter, provide pitch, P, of about 0.72 inches, and vertical resolution about 0.48 inches. Then, an image-generating computer (not shown) such as the host computer 370 generates an 28 image in the manner such as described for the detector configuration illustrated in FIG. 1A.

Further, in an alternative embodiment of the present invention, each of the detectors is equipped with a radiation collimator in the path of the incoming source radiation. Also to reduce the unwanted background of gamma-rays scattered by the target, e.g., truck, and by the ground, i.e., when the impinging fan beam strikes the ground, the detector array is surrounded by, for example, lead shielding. This shielding and collimation improves the image crispness and depth of radiation penetration. The lead shielding or similar shielding may surround the entire detector array or alternatively, may be place around the individual detectors within the detector array.

In an alternative embodiment, a filter, e.g., a thin lead gamma-ray filter, is positioned over the detector array to selectively block out those Cs-137 (or Co-60) gamma rays that have been scattered by the target, and that have been significantly reduced in energy. By blocking out this unwanted background radiation, i.e., noise, image crispness and penetration are enhanced. Alternatively, filters may be positioned over less than the entire detector array, depending on the areas of the area most affected by unwanted radiation.

In the stationary-target mode, the truck 16' scans the target object 10 while the target object is stationary and without an occupant, while the truck 16' moves along a length of the fast-moving target object 10 to produce a full image of its contents. Advantageously, the truck 16' need not move at exactly the same speed during the entire scan because the time constant $T_c$ between which detector readings (photon counts) are recorded is varied as a function of the velocity of the truck (which is monitored by the image-generating computer, which receives a velocity signal from speedometer equipment aboard the truck), in order to maintain a substantially constant horizontal pixel width $\Delta x$.

Optionally, in the alternate moving target mode, the truck 16' is stationary and the occupant of the target object 10' drives the target object 10 just past a source fan beam region 320' to avoid the radiation. The shutter (not shown), such as described earlier, is then opened and the occupant drives the fast moving target object 10 at about a nominal rate of acceleration which has been clocked at about 33 inches/sec².

While the fast-moving target object 10 is accelerating, a velocity measuring system (such as one of the velocity-measuring systems described hereinabove), such as shown and described in reference to FIG. 1, or such as a high repetition conventional radar range as mentioned earlier herein, is aimed at the target object 10 and measures position data thereof several times per second. The position data is sent to an image-generating computer (not shown), such as the host computer 370 shown in FIG. 3.

The position data, together with time data, is next converted into velocity data by the image-generating computer (not shown) to form a velocity profile v(t). Simultaneous with the acceleration of the target object 10, the image-generating computer starts to generate an image of the target object 10 in real-time, by setting a count time $T_c$ (as defined earlier) for each detector equal to a time required for the fast-moving target object 10 to move the fixed distance of the horizontal grid unit size, $\Delta x$ ($\Delta t = \Delta x/v$) described earlier, wherein $\Delta x$ is preferably set to equal the vertical grid unit size $\Delta y$ and wherein $\Delta y$ is proportional to the detector pitch P, previously defined as center-to-center vertical distance between neighboring detectors 26 or staggered detectors 202. The proportionality of $\Delta y$ to pitch P has been previously described herein.

The moving target mode of operation requires as little as about 6 seconds to fully image the fast-moving target object 10 for an accelerating vehicle. In the stationary target mode of operation, the fast-moving target object 10 can be inspected at about 5 miles/hour or greater, while the mobile system 300' maintains the horizontal and the vertical resolution (grid unit) for imaging of about 0.5 inches, in accordance herewith.

Employing any of the above-cited velocity measuring systems enables the mobile system 300' to scan and image at a variety of variable speeds and accelerations while still maintaining excellent imaging resolution, and distortion-free images, at ultra high speeds (relative to heretofore known imaging approaches) such as up to about 60 miles per hour.

Advantageously, therefore a velocity of the target object 10 or a mobile system can be selected and adapted according to the mission at hand. As the target velocity increases, for a similar configuration of the 30 source 18, 181 and the detector array 14, 14', a color or gray-scale tone definition per pixel, or the number of colors which that pixel can have, effectively decreases accordingly. This decrease in color definition per pixel occurs because as the target velocity increases, a number of photons reaching the detector 26 in the detector array 14 decreases, since a count time $T_c$, is decreased, as it takes less time for a target length corresponding to one pixel to pass the detector 26. Since there are less overall photons to count, (a smaller number of counts/pixel), the counts can be distributed among fewer colors or gray-scale tones than if there were a higher count rate.

Accordingly, if a high throughput is required a higher target or mobile system velocity may be selected, sacrificing some color definition as described above. Otherwise, if a higher color definition image is required, such as for disarming an explosive device, a lower target or mobile system velocity may be selected.

Furthermore, in cases involving stolen vehicle detection, where high throughput or speed is of the highest importance and image resolution is not as important, and where there are three (3) rows of detectors 202, such as shown in FIG. 6, two (2) of the three (3) rows of detectors 202 may be ignored for imaging (thereby reducing image resolution, i.e., increasing grid unit size of a pixel) in the interest of speed or processing time.

Referring next to FIG. 4, a block diagram is shown of the systems of FIGS. 1 and 2 showing gamma/x-ray detectors coupled through 16-channel processing units, accumulators, RS-485 line drivers, and an RS-485 interface card to a computer, wherein the computer processes discrete photon count information received from the detectors 26 and causes a display device to display an image of the contents of a target object 10, such as the tanker truck of FIG. 1, or FIG. 2 in response thereto.

The detector array 14 is depicted in FIGS. 1 and 2, as are the electronics 22 and the graphical display device 24. The detector array 14 employs the plurality of gamma/x-ray detectors 26. The gamma/x-ray detectors 26 are coupled in groups of 16 gamma/x-ray detectors each to accumulators, which are in-turn coupled to 16-channel data processing circuits 30. In practice, the number of gamma/x-ray detectors 26 used depends on the height of the vehicles to be inspected and the desired resolution, i.e., number of pixels, in the image desired.

In one embodiment, especially favorable for detecting car-sized objects (e.g., stolen cars) within a vehicle, a cargo container, or a railroad car, 48 gamma/x-ray detectors are employed in a linear vertical fashion and a grid unit size or resolution of about 2.5 inches is selected.

In another embodiment, especially favorable for faster-moving targets, the detector array 14 comprises 64 detectors 26 with a pitch of 1.76", the detectors 26 being sampled at 600 times per second (sampling every 1.7 msec per detector) corresponding to a speed of 60 mph of the fast-moving target object 10.

In another variation, especially favorable for finer spatial resolution, referred to as VACIS-II, three (3) vertical rows of 112 detectors 26 each, (336 detectors 26) are employed and a vertical and horizontal resolution of about 0.4 inches is selected.

The 16-channel data processing circuits 30, each include an accumulator 47, the 16-channel data processing circuits 30 being coupled to an RS-485 line driver/firmware ("driver/firmware") 32, which is coupled to an RS-485 interface (or RS-485, card) 34. The RS-485 32 interface 34 is embodied on a circuit card located within a computer system 36. A suitable RS-485 interface is available as Model No. 516-485, Part No. 3054 from Sea Level Systems, Inc., and from numerous other vendors under respective model/part number designations.

The computer system 36, which is preferably a Pentium-300 based personal computer system, or a faster (newer) computer system, operates programmatically under the control of a software system.

The computer system 36 receives data on velocity from a velocity measuring device 35, such as any of the devices described herein (see FIG. 1, FIG. 3), and uses the velocity data to adjust the count time is as previously defined herein (as a sample period for the detectors 26).

The computer system 36 also receives information on an accumulated photon count from the accumulator 47 through the driver/firmware 32 (described later) originating initially from detector pulses from each of the 16-channel data processors 30, in response to the detection of individual photons by the gamma/x-ray detectors 26, 202 (FIGS. 1, 1A and 2). As explained in further detail herein below, the software system accepts a value of the accumulated photons counts passed to it by a discriminator 44, which ensures each pulse height, from energy deposited in the detector by the photons, is above an electronic noise level. Advantageously, the accumulated photon counts permits for a noiseless signal, as compared to measuring current from many more photons which has associated current noise, because each photon is counted above a noise threshold. The software system generates a radiographic image-like display output signal in response to the accumulated counts.

The radiographic, image-like display output signal generated by the composite software is coupled to 33 the graphical display device 38, which is preferably a Super-VGA monitor, and is used by the graphical display device 38 to generate a graphical representation of the densities within the vehicle under inspection.

Unlike some prior art systems, which do not generate a graphical representation, i.e., a "picture" of the densities of the contents of the vehicle under inspection, the present embodiment generates such a picture.

In addition, unlike prior art systems, in this particular embodiment, each vertical line composing this picture is generated sequentially in real time, while the fast-moving target changes position relative to the source 18 and to the detector array 14.

Advantageously, this allows for easy instantaneous, direct visual interpretation of the results of the scanning of the vehicle under inspection making possible prompt interdiction of the vehicle before unloading the contraband, as opposed to interpreting more subtle indications of the densities within the vehicle under inspection as may be required in prior art systems.

Advantageously, the preferred software system also causes the display of a reference image simultaneous with the image generated in response to the vehicle under inspection, so that an operator of the present embodiment can easily make a visual comparison between what a vehicle of the type being inspected should "look like", and what the vehicle under inspection actually "looks like". Such "side-by-side" inspection further simplifies the detection of contraband using the present embodiment.

As a result of the very low intensity gamma-ray or X-ray radiation used by the present embodiment, photon penetration, as opposed to backscatter, can be used to generate a side, as opposed to a bottom/top, image of the vehicle under inspection, because a radiation exclusion zone is small for a low-intensity field. This represents a significant improvement over prior art systems wherein a bottom/top presentation of the radiation source is required to avoid the need for excessive radiation shielding, but dictates that the vehicle s frame, drive train, wheels, etc., interfere with the density measurements taken based on radiation penetration. Backscatter-type density measurement systems are less accurate due to the non-uniform backscattered radiation on which they rely for density measurement. In addition, backscattered photons have significantly decreased energy, and are less penetrating and cannot effectively measure high pressure tanker trucks with double-walled thick steel walls.

Figure 5:
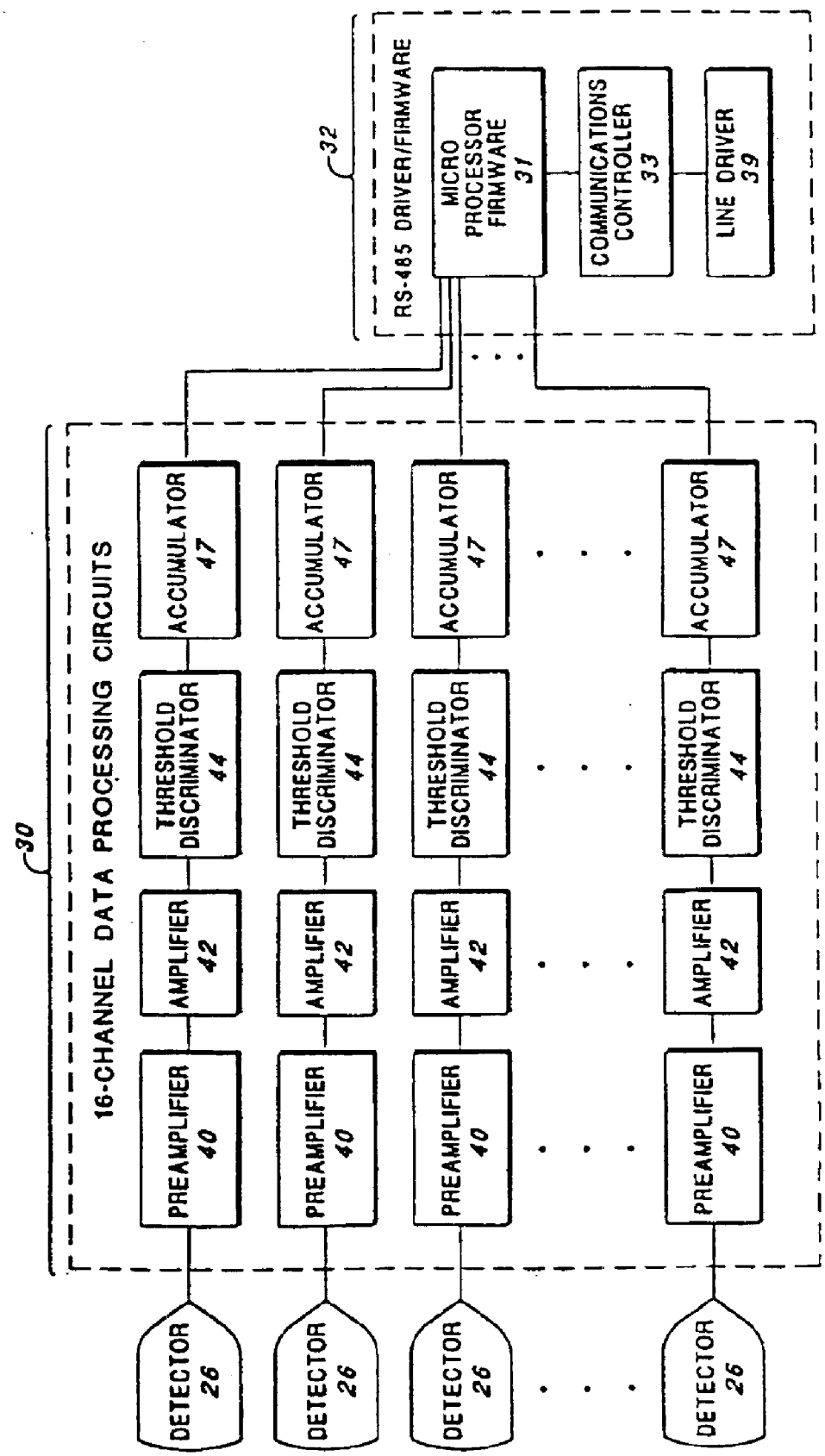
FIG. 5 is a block diagram showing the detectors of FIGS. 1 and 2 coupled through preamplifiers, amplifiers, discriminators, accumulators, and an RS-485 line driver that make up one embodiment of the 16-channel 5 processing units of FIG. 4.
Figure 6A:
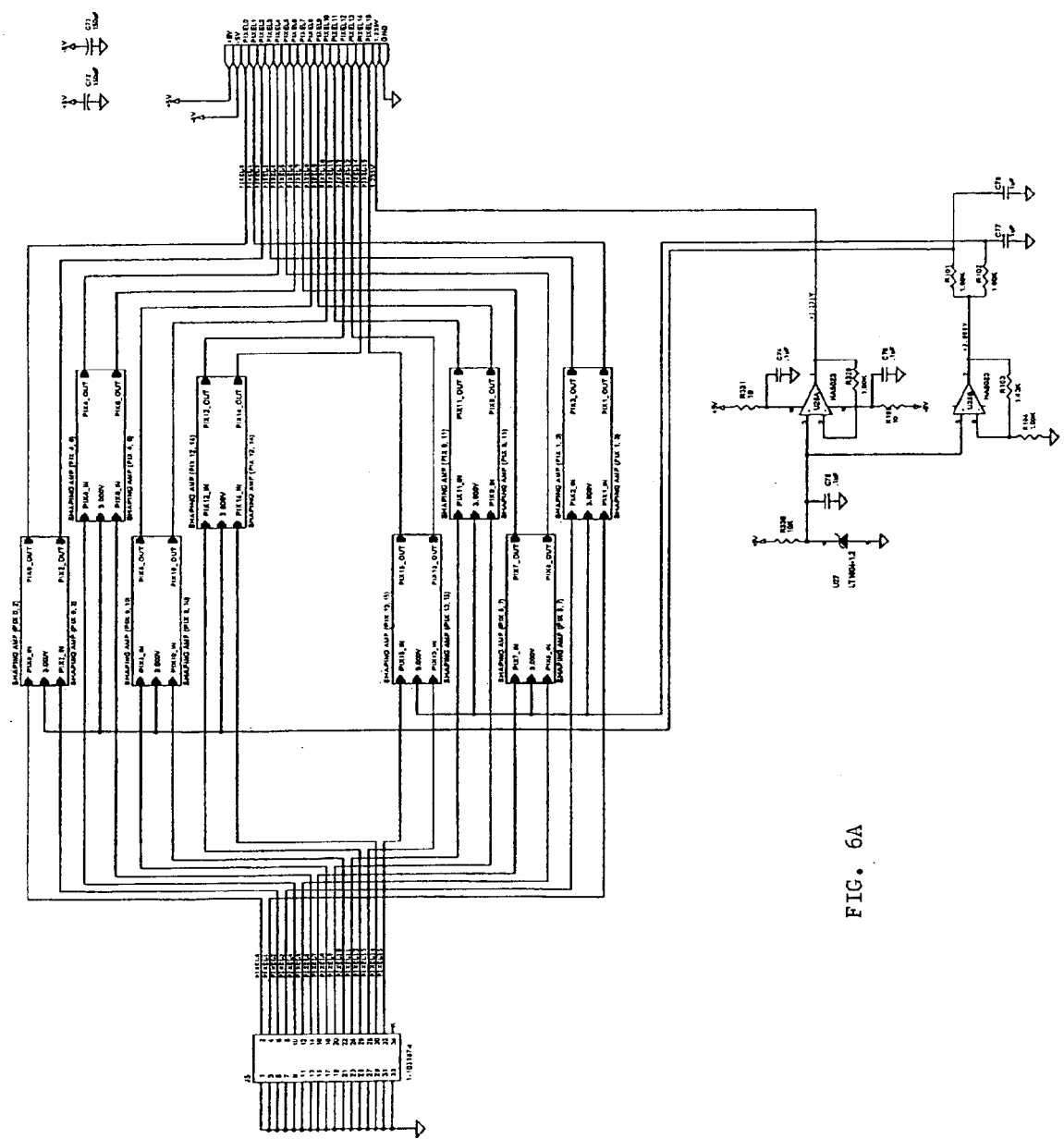
FIGS. 6A, 6B, 6C, 6D, 6E and 6F are schematic diagrams showing one variation of an analog portion the 16-channel processing units of FIG. 4.
Figure 6B:
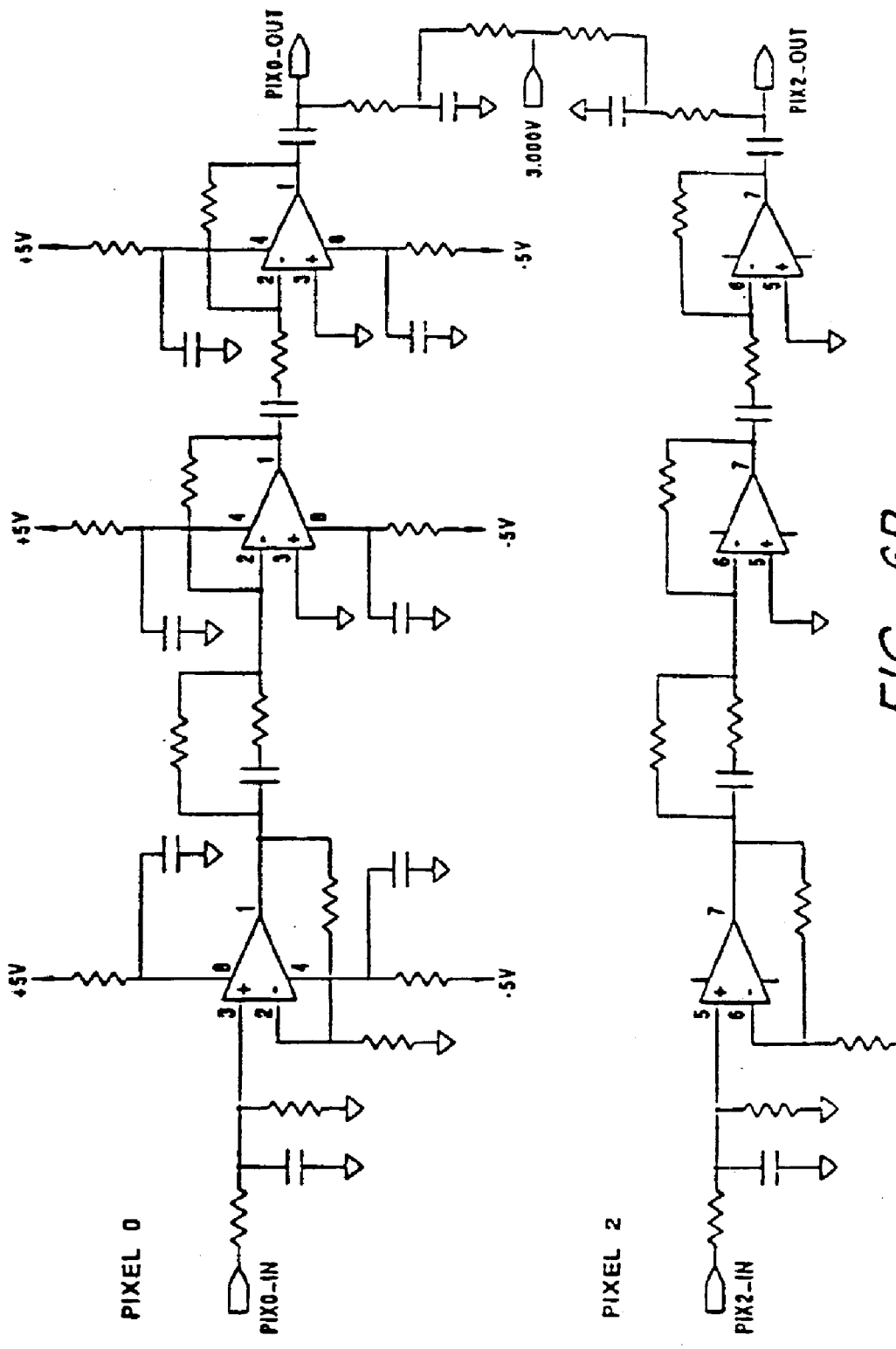
Figure 6C:
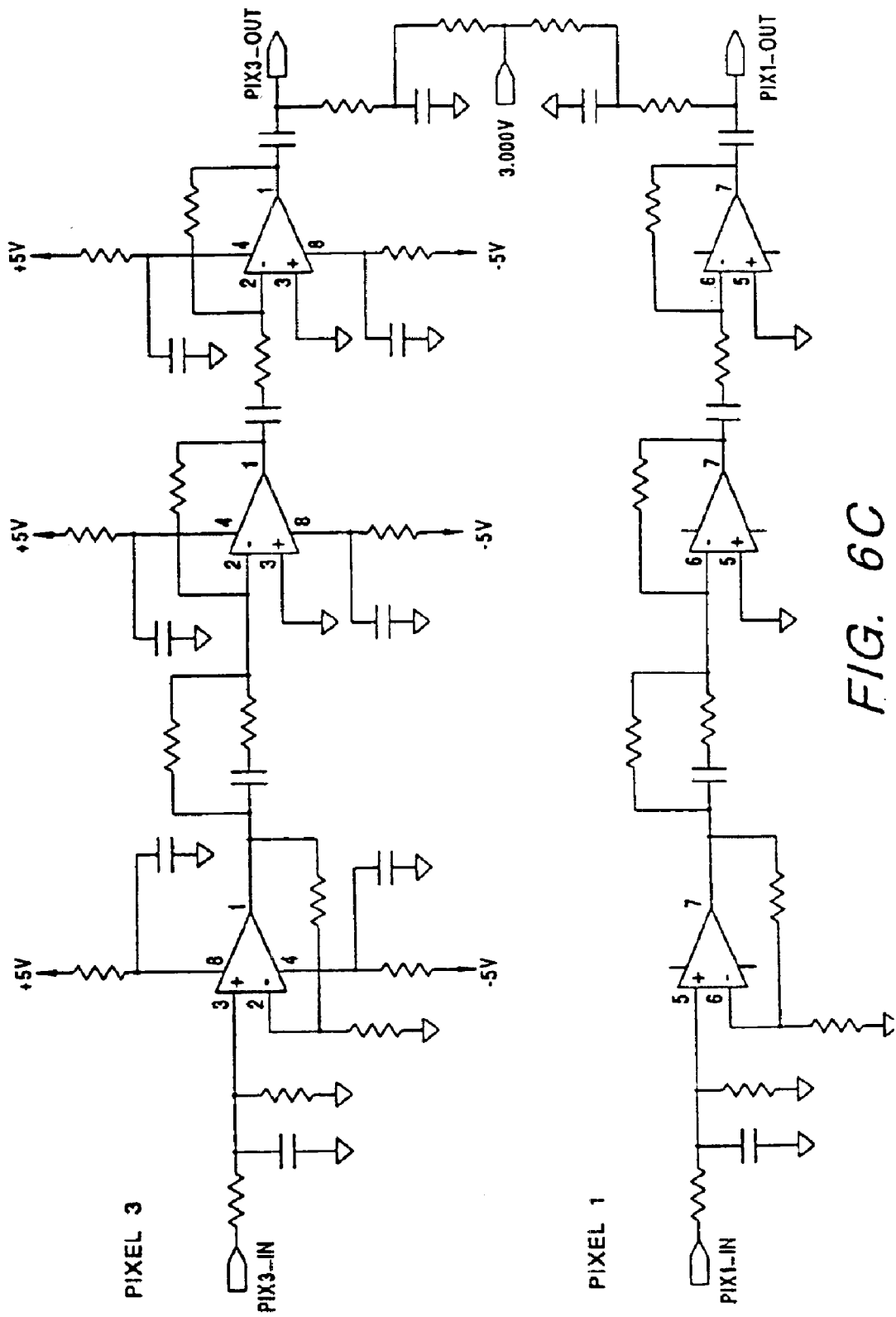
Figure 6D:
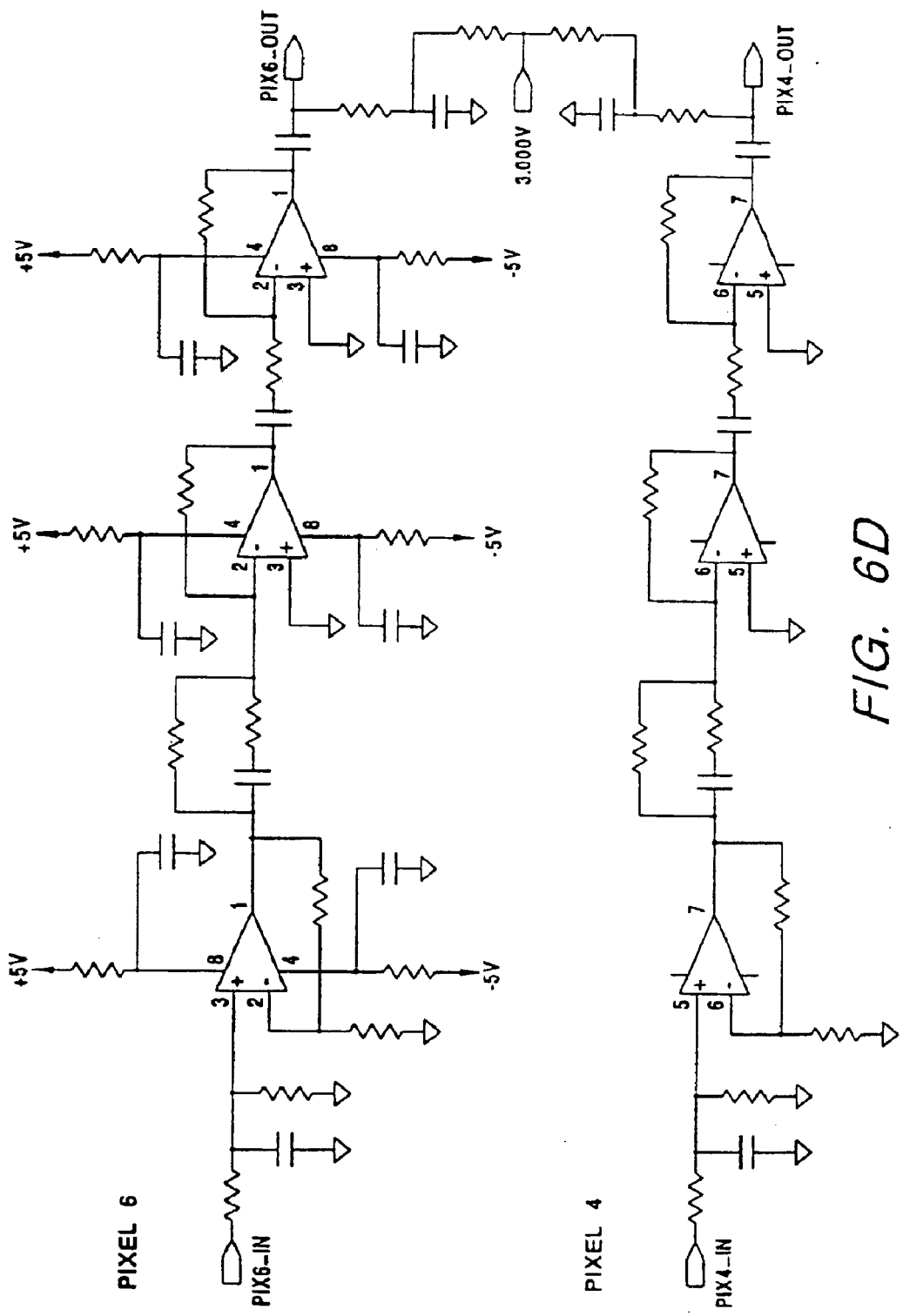
Figure 6E:
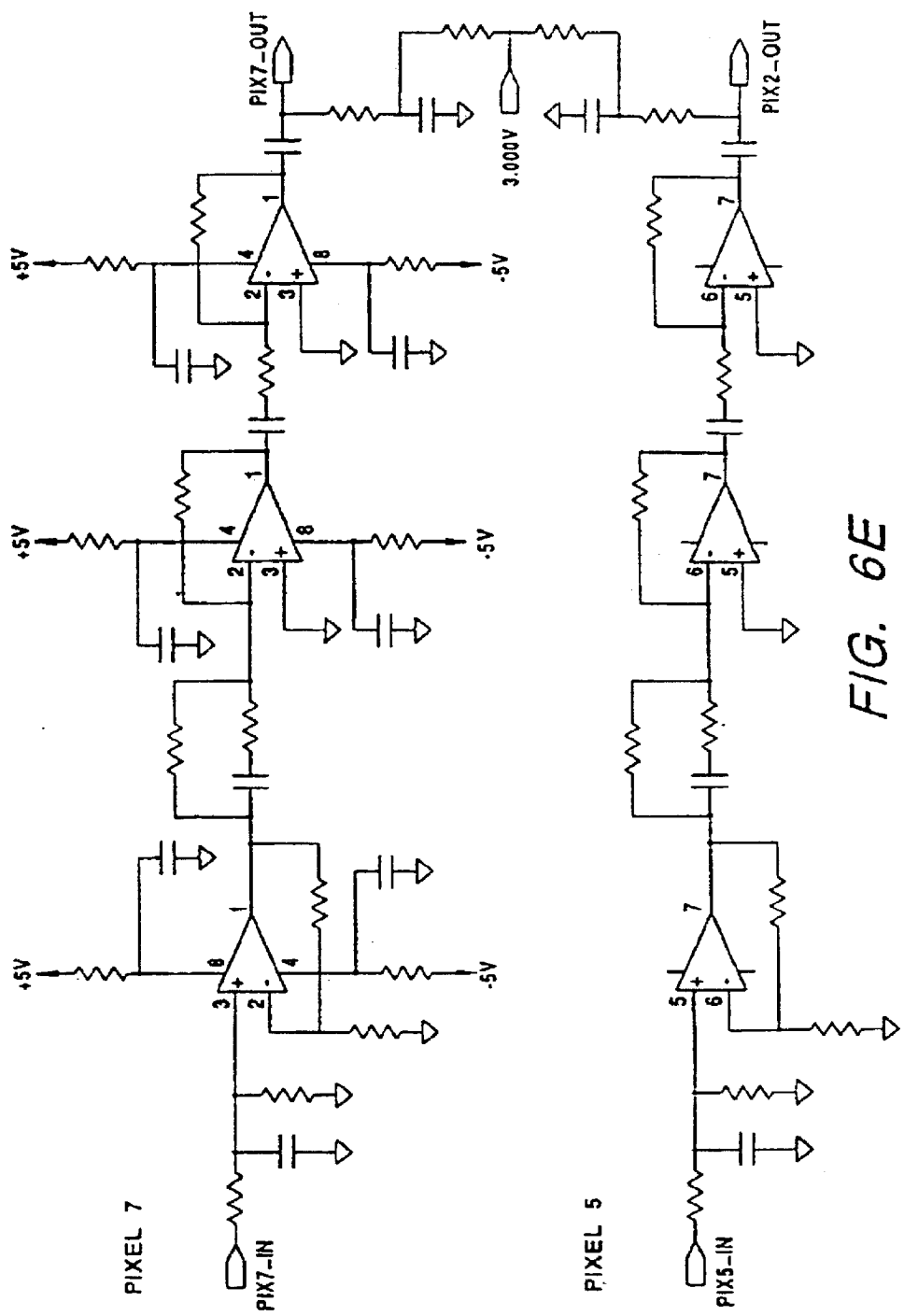
Figure 6F:
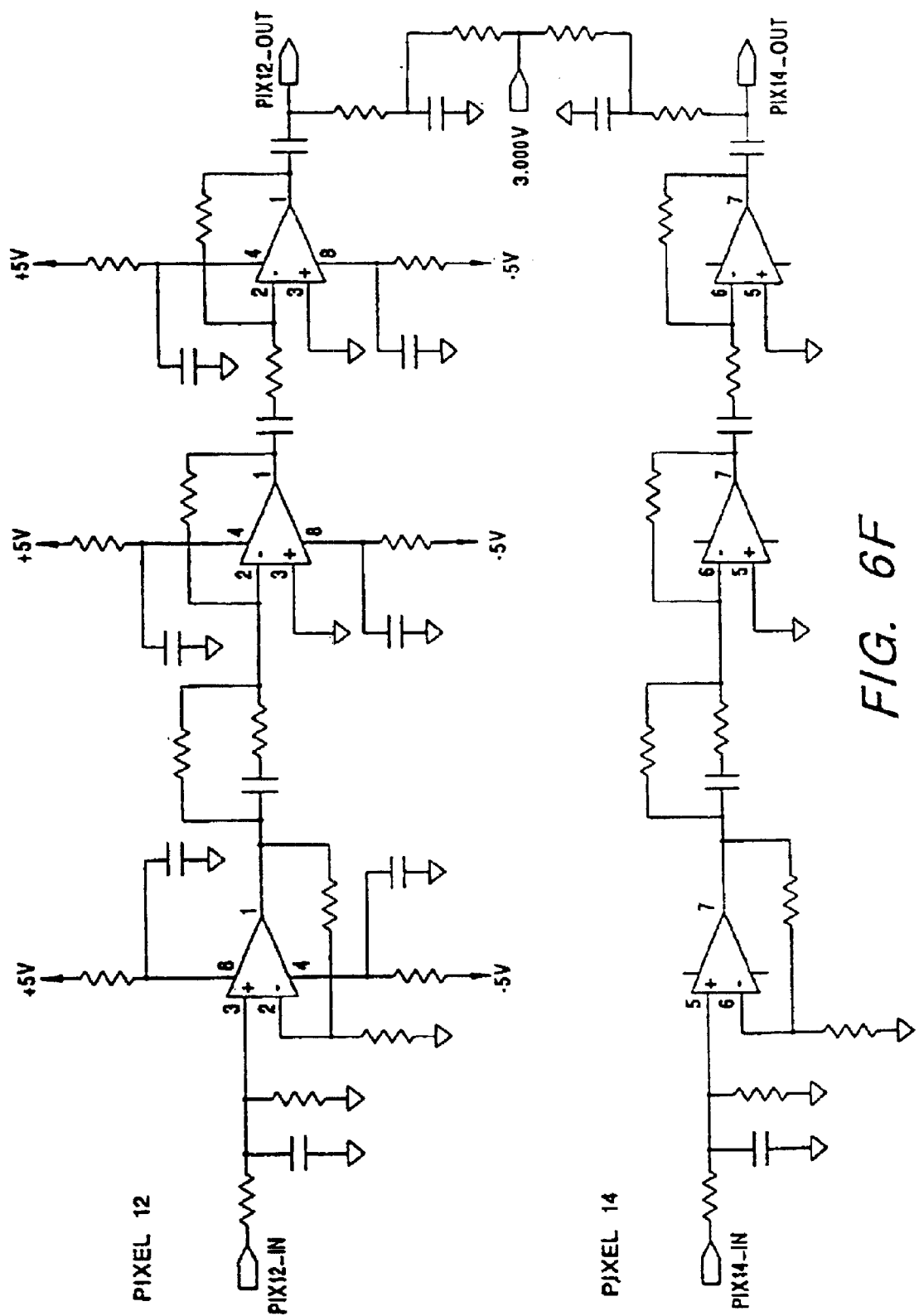

Referring next to FIG. 5, a block diagram is shown of the detectors of FIG. 4 coupled through preamplifiers 40, amplifiers 42, threshold discriminators (discriminators) 44, accumulators 47, and an RS-485 line driver/firmware 32, that make up one embodiment of the 16-channel processing units of FIG. 4. The RS-485 driver/firmware 32 comprises microprocessor firmware 31, a communications controller 33 and a line driver 39.

Each of the radiation detectors 26 is coupled to a preamplifier 40 within the 16-channel data processing unit 30. Each preamplifier 40 is coupled to an amplifier 42, which is in turn coupled to a discriminator 44. Each discriminator 44 generates an electrical pulse for each photon detected above an electronic noise level by the radiation detector 26 coupled thereto.

Advantageously, the use of (non-integrating) discrete photon counting at the levels of photon fluxes employed herewith (i.e. relatively very low radiation intensity) together with the use of the discriminator 44 to allow photons (or pulses) to be counted only above a cut-off threshold energy, allows for a much improved, virtually noiseless system, using lower strength sources than conventionally used.

In accordance herewith, except for a relatively low natural-background countrate, every pulse generated from the discriminator 44 represents an actual photon from the radiation source 18, 18'.; that is, almost exclusively, photons generated from the radiation source 18, 18' are counted at the accumulators 47. Since nearly every pulse counted at the accumulator 47 represents an-actual photon from the radiation source 18, 18', a photon-by-photon count (or 10 count rate) at the accumulator 47 represents a virtually noiseless signal of how many photons from the radiation source 18, 18' hit each detector 26.

This photon-by-photon virtually noiseless signal has several advantages over some prior arts systems wherein photon-integration over a myriad of photon energy levels is employed. Even with such prior art, or state of the art integrating discrete photon counting systems (such as may be used with standard X-ray detectors) it is necessary to bombard the detector 26 with many more orders of magnitudes of photons in order to drown out a substantial noise contribution (e.g., leakage current) of a signal.

Problematically, because so many more orders of magnitudes of photons are necessary to obtain the signal with an integrating discrete photon detector, a common method of integrating a detector count (or count rate) is to generate a current from charge collected as a result of energy being deposited in a crystal of the detector 26, rather than to count the pulses generated for each photon deposited in the detector 26. The strength of the current is then measured, in the conventional systems, instead of the total number of photon counts in accordance with the present invention. From this current must be subtracted a varying (temperature dependent) background current.

Another further problem with this form of integration, is that there is always some parametric leakage current involved in a circuit or a solid state device measuring the current, and this further contributes to the noise of the signal, worsening the initial problem.

With the prior integrating discrete photon counting systems, not only more photons are needed, but also a much higher source strength and a much longer inspection time is needed in order to generate enough photons necessary to do the integration or to generate the current from the induced charge created by the energy deposition of the photons. This is also problematic because a higher source strength means higher doses of radiation, and additional power and expense.

Therefore, preferably, a mono-energetic source such as a 662 keV gamma-ray source of Cs-137 or a near monoenergetic source such as Co-60 (dual energy, one energy level at 1170 keV and another at 1330 keV) is employed to make discrete photon counting at the threshold cut-off energy level or narrowband much easier, since the radiation source 18 is constant with time and need not be filtered to filter out a soft, lower energy component.

Alternatively, in accordance herewith, any source could be used in conjunction with a filter placed around the radiation source 18, 18', filtering out photons of energies outside a desired energy level.

Because very low intensity gamma-ray or x-ray radiation is used with the present embodiment, pulse pileup is generally not of significant concern. Count rates of up to 90,000 counts/seconds are presently being counted with negligible "chance coincidence" loss with pulse amplifiers capable of counting nearly two million counts/seconds (via 40 nanosecond amplifier "pulse" time constants).

The discriminators 44 within each of the 16-channel data processing units 30 are coupled through the accumulator 47 to a line driver/firmware (RS-485 driver/firmware) 32 which includes a microprocessor firmware (processor) 31 coupled at an output to a communications controller 33 coupled at an output to a line driver 39. Each of the 16-channel data processing units 30 includes its own line driver/firmware 32.

The line drivers/firmware (RS-485 primer/firmware) 32 operate under the programmatic control of a firmware operating system in the processor 31 which processor 31 also controls the communications controller 33 and the line driver 39, such as shown in APPENDIX A.

In operation, the preamplifiers 40, and amplifiers 42 function in a conventional manner to amplify signals generated by the detectors 26 connected thereto. Outputs of the amplifiers 42 are passed along to the discriminators 44, which accept pulses that are well above a noise threshold (e.g, about twice the noise threshold). The pulses are passed by the discriminator 44 and then counted in an accumulator 47 for each detector 26, resulting in accumulated counted pulses (accumulated pulse counts), thereby generating a count rate as previously discussed.

The line driver/firmware 32 passes the accumulated pulse counts, which pulses are accepted past a threshold by each of the discriminators 44 and passed to each accumulator 47, within a particular 16-channel data processing unit 30, along to the computer via the RS-485 interface 34 illustrated in FIG. 4.

Referring next to FIGS. 6A, 6B, 6C, 6D, 6E and 6F, schematic diagrams are shown of one variation of an analog portion the 16-channel processing units of FIGS. 4 and 5. The schematics of FIGS. 6A, 6B, 6C, 6D, 6E and 6F are self-explanatory to one of skill in the art of 38 circuits and therefore further explanation of these figures is not made herein.

Figure 7A:
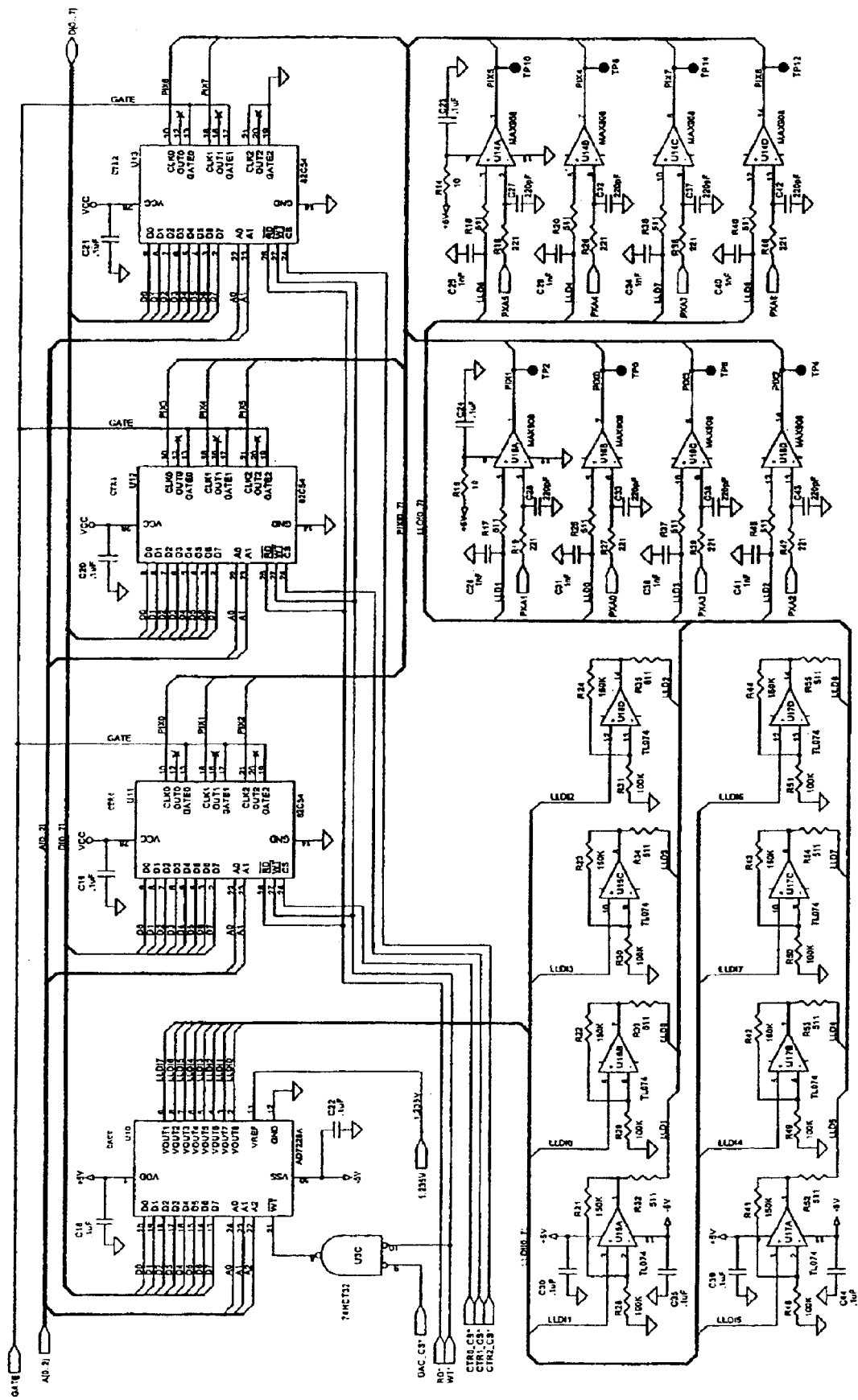
FIGS. 7A and 7B are schematic diagrams showing one variation of a digital portion of the 16-channel processing units of FIG. 4.
Figure 7B:
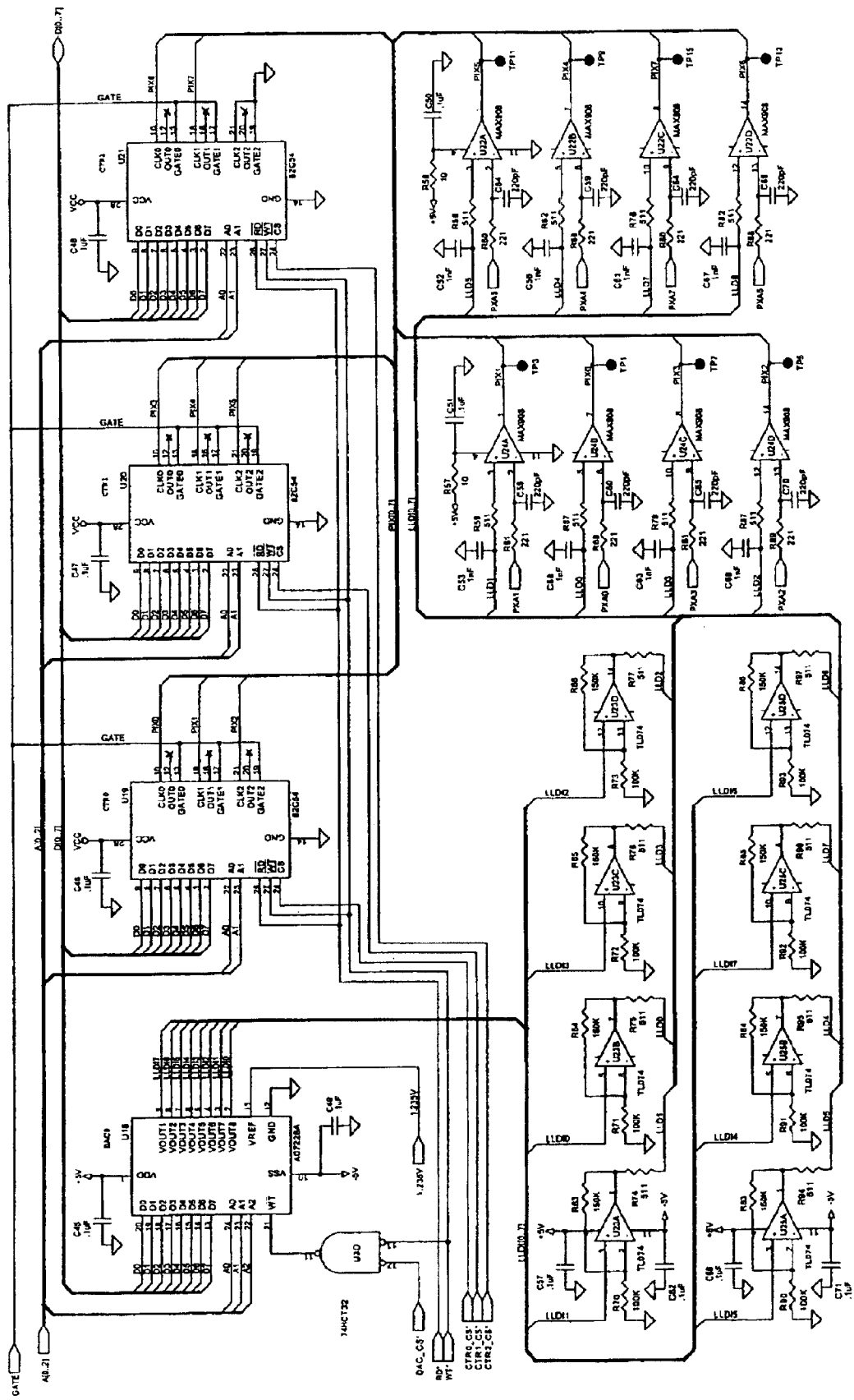

Referring next to FIGS. 7A and 7B, schematic diagrams are shown of one variation of a digital portion of the 16-channel processing units of FIGS. 5 and 6. The schematics of FIGS. 7A and 7B are self-explanatory to one of skill in the art and therefore further explanation of these figures is not made herein.

Figure 8:
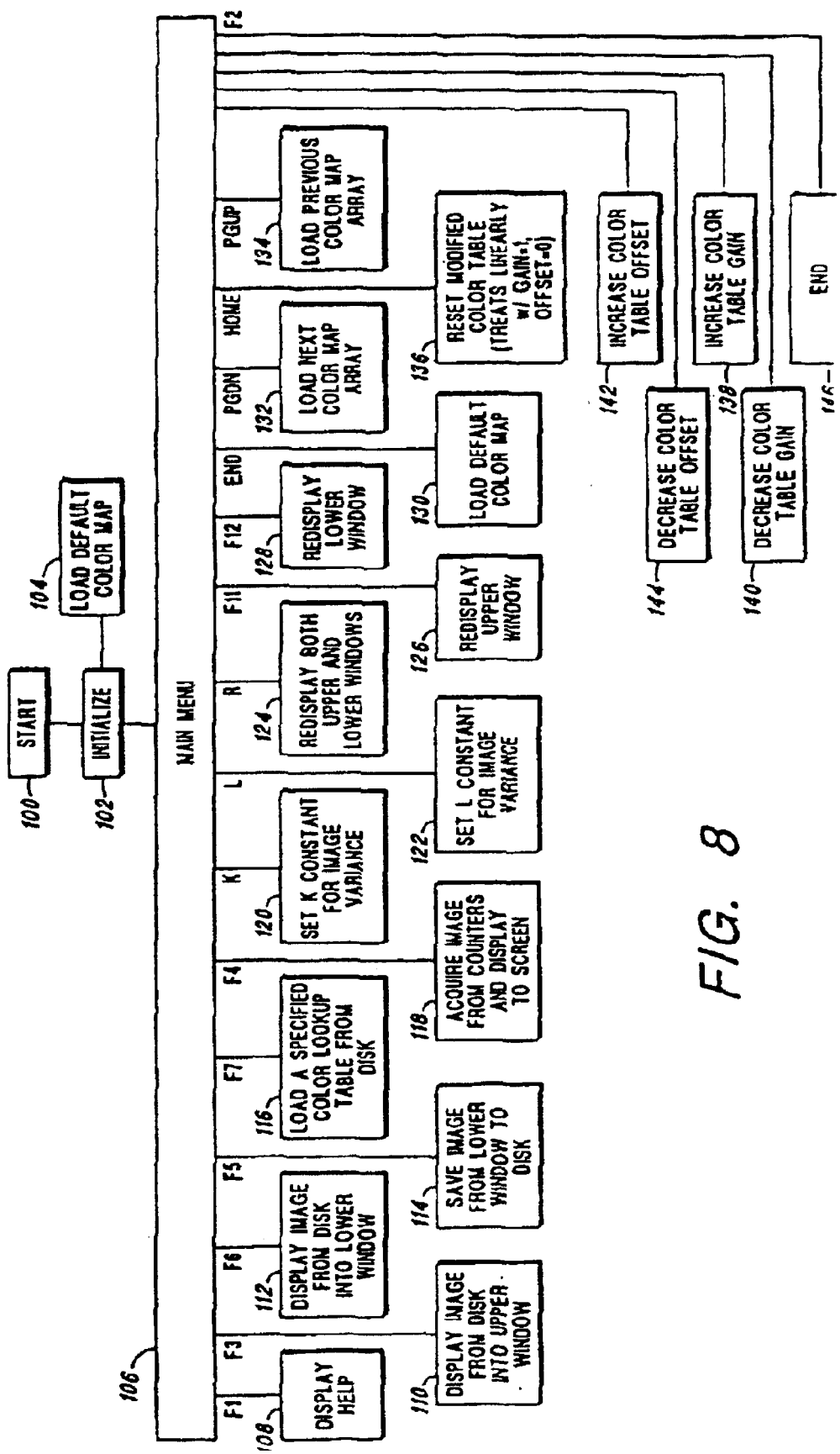
FIG. 8 is a block diagram of functional components that make up one embodiment of a software system with which the computer of FIGS. 1 and 2 is controlled.

Referring next to FIG. 8, a block diagram is shown of functional components that make up one embodiment of a software system with which the host computer 370 of FIG. 4 is controlled. Upon initialization (Block 100), the computer, under control of the software system, initializes (Block 102), and loads a default color map display (Block 104), which maps detected densities within the vehicle under inspection, i.e., pulse counts, to specific colors to be produced on the display device 38 (shown in FIG. 4). Next, the user is presented with a main menu (Block 106), and the computer is instructed to wait until an operator instructs the software system as to what step to take next.

One of the options available to the operator is a help function (Block 108). The help function displays tutorial and/or reference information to the operator via the display device, as is common in the computing arts.

Another option presented to the operator is the "Display Image from Disk in Upper Window" option (Block 110). When selected, this option allows the operator to load a saved display image from a hard or floppy disk drive within the computer, and to automatically display the image in the upper display window on the display drive. (See FIG. 10) Generally, the upper display window, in accordance with the present embodiment, is used to display a reference image, i.e., an image of the 39 same make of truck under inspection, but while empty, i.e., containing no contraband.

A further option that can be selected by the operator is a "Display Image from Disk in Lower Window" option (Block 112). When selected this option allows the operator to load a saved image from a hard or floppy disk drive within the computer, and automatically displays the image in the lower display window on the display drive. (See FIG. 10) Generally, the lower display window, in accordance with the present embodiment, is used to display an inspection image, i.e., an image of the vehicle under inspection. A useful function of this option is for reinspection of a vehicle at a later time by a supervisor in order to maintain quality control. Because the image is stored on disk, it is not necessary that the vehicle be present when this re-inspection takes place. The saved image of the vehicle, after being loaded, can easily be visually compared with the reference image loaded into the upper display window.

The next option available to the operator is the "Save Image from Lower Window to Disk" option. This option can be used to save an image of a vehicle under inspection for later reinspection, or can be used to save a reference image after a known empty vehicle has been inspected, i.e., scanned using the present embodiment.

Using a "Load Color Lookup Table from Disk" option (Block 116), the operator is able to load a previously saved color lookup table from disk. This allows the user to retrieve a color map, different from the default color map, so that a different set of colors can be mapped to various density measurements, i.e., pulse counts within the vehicle.

The next option is the "Acquire Image from Counters and Display to Screen" option (Block 118). This option initiates an image generation program, as described below in reference to FIG. 9, which causes the detector array 14 and the radiation source 18 to perform density measurements and causes the display of an image indicative of the various densities within the vehicle under inspection in the lower display window on the screen display. Advantageously, the present embodiment allows the operator to display a reference image in the upper display window while the inspection is being conducted, so that he or she can visually compare what the vehicle under inspection should look like empty with what the vehicle under inspection in fact looks like. In this way, the operator is able to determine whether or not the vehicle under inspection may contain contraband.

The next two options (Blocks 120 and 122) allow the operator to set values for what is referred to herein as the "K" constraint and the "L" constraint. These two "constraints" function in a manner similar to the well known functioning of the brightness and contrast controls on commonly available cathode ray tube-type displays. These values affect the mapping of colors to the various pulse counts, which is performed as follow:

(1) a "white" level, i.e., a number of counts corresponding to zero density, is determined for each sensor during detector calibration, which is a step in image acquisition as described below in reference to FIG. 7;

(2) the variable "T" is then set equal to this white level times the reciprocal of the number of photons counted by a particular detector at a particular horizontal position on the vehicle;

(3) if "T" less than one, i.e., more photons are counted than the white level, then T is set equal to one;

(4) the variable "D" is then computed as follows:

$$D=254/(1+L)\ln(T^*K),$$

where L and K are the constraints mentioned above, which are initially set to one, and where T is defined above; and 5) if "D" is less than 1 or greater than 254, then D is set to 1 or 254, respectively.

The significance of the number 254 in the above computations is that there are 256 possible colors displayable on the preferred Super-VGA display device, however this number could be adjusted up or down to yield an appropriate color mapping where more or fewer colors are displayable.

Other options available to the user are options to "Redisplay Both Windows" (Block 124), "Redisplay the Upper Window" (Block 126) and "Redisplay the Lower Window" (Block 128). Redisplay options such as these are useful to the operator if the images displayed on the display device 38 become corrupted in some way, as for example may occur if text is sent to the display device 38 while it is displaying a graphical image.

The user may also "Reset a Default Color Map Array" (Block 130), "Load a Next Color Map Array" (Block 132) and "Load a Previous Color Map Array" (Block 134). These options are used to step through various preconfigured color maps, and to reestablish the default color map, so that the operator can utilize a color map that best emphasizes the features of the vehicle under inspection that he or she is inspecting.

Other options available to the user are to "Reset Modified Color Table" (Block 136), "Increase Color Table Gain" (Block 138), "Decrease Color Table Gain" (Block 140), "Increase Color Table Offset" (Block 142), and "Decrease Color Table Offset" (Block 144). These options affect the "mx+b" relationship between the photon counts determined by the gamma/x-ray detectors and 42 the colors displayed on the display device. The "gain" (m) is initially set, or can be reset, to one, and the "offset" (b) is initially set, or can be reset, to zero. These two parameters allow the operator to "zoom" in on a particular range of densities for mapping within the color table by increasing or decreasing the offset in order to establish a minimum density of interest (with every density below this density being mapped to zero density (or "white"), and by increasing or decreasing the gain in order to establish a maximum density of interest (with every density above this density being mapped to maximum density (or "black").

A final operator-selectable option depicted in FIG. 8 is an "End" option (Block 146). This option is used by the operator to exit the software system and to return control to an operating system, such as is known in the art of computer technology.

Figure 9:
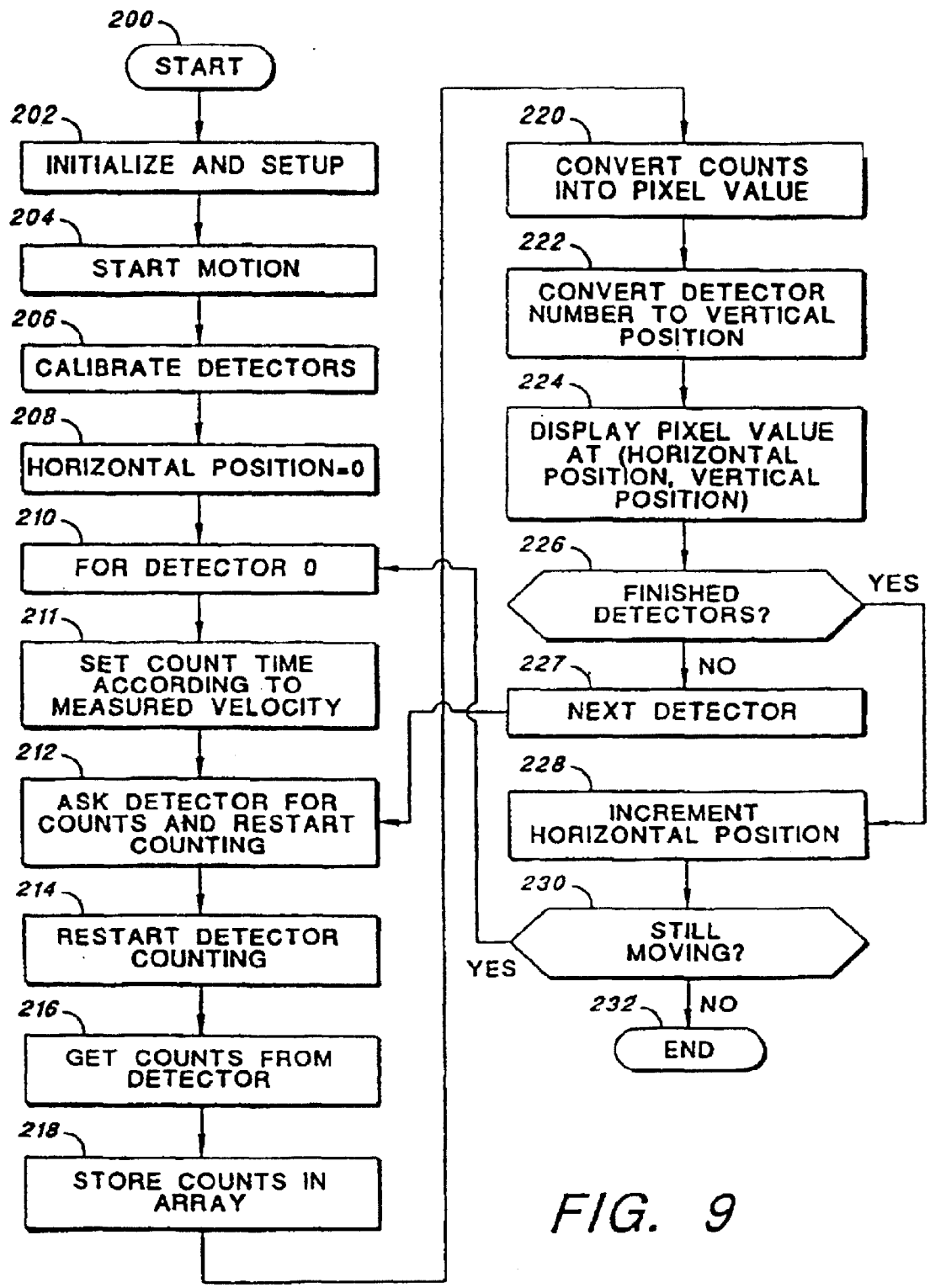
FIG. 9 is a flow chart showing the steps traversed by the computer of FIGS. 1 and 2 in response to the software system of FIG. 7 when an image generation program is executed.

Referring next to FIG. 9, a flow chart is shown of the steps traversed by the computer 36 of FIG. 4 in response to the software system of FIG. 8 when an image generation program is executed.

Upon being initiated (Block 200), the image generation is initialized (Block 202), and the movement of either 1) the radiation source truck 20, and the detector array truck 16, if used, or alternatively, 2) the movement of the mobile system 300' in another embodiment, or 3) the movement of the target object 10, is initiated (Block 204). Next, the detectors 26 are calibrated (Block 206) by irradiating the detectors with the radiation source 18 at a point along the track before the radiation source 18, 18' and the detector array 14, 14' become aligned with the vehicle or the target object 10, to be inspected, such that a horizontal length of the target object will be traversed upon continuation of the initiated movement, e.g., before the vehicle under J 43-inspection is interposed between the detector array 14, 14', and the radiation source 18, 18'. Such irradiation of the detectors 26 establishes a baseline of radiation (or "white" photon count level) corresponding to a density in the vehicle being inspected of approximately zero density and corresponding to a maximum photon count. Three photon counts are made in this manner for each detector 26. Such counts are then arranged for each detector 26 and then stored in an array having a white level element for each detector 26.

A horizontal position is then set to zero (Block 208). The horizontal position corresponds to a position along the track or a mobile system path or a target object path arbitrarily selected to be a first position at which density measurements are taken. Irrespective of which embodiment is employed or which reference is moving (the detector-source, or the vehicle or target object 10), this horizontal position should be at a point before the vehicle is interposed between the detector array 14 and the radiation source 18.

Next, a detector count is set to zero (Block 210), which corresponds to a first of the detectors 26 in the detector array 14 to be queried for a photon count. If the target object 10 is moving, a velocity of the target object 10 is measured by any of the several methods described earlier, herein, and a count time per grid unit is set (Block 211) according to the measured variable velocity of the target object to effect a desired mapped grid unit size without distortion. Next, this detector is queried for a photon count and is instructed to restart counting photons (Block 212). In response to this instruction, the detector queried restarts counting photons (Block 214) and the previously determined number of photon counts is passed along to the computer (Block 216). This number of photon counts is 44 stored into an array within a memory in the computer (Block 218) and is then converted into a pixel value (Block 220). Conversion into the pixel value includes mapping the number of photon counts to a color to be displayed on the display device. Such mapping is described more completely above in reference to FIG. 8.

Next, the detector number queried is converted into a vertical position on the screen display (Block 222) and the horizontal position of the radiation source 18, 18' or the mobile system path or the target object path and the detector array 14, 14' along the tracks is converted to a horizontal position on the screen display. Next, the pixel at the determined horizontal and vertical positions is illuminated using the color corresponding to the number of photon counts, as previously converted (Block 224).

Next, a determination is made as to whether all of the detectors 26 in the detector array 14 have been queried for a number of photon counts for the current horizontal position (Block 226). If all the detectors have not been queried (Block 226), the detector number to be queried is incremented (Block 227) and execution of the image generation program continues by querying the next detector in the detector array 14 for the number of photon counts, and by instructing such detector to restart counting (Block 212). Execution continues from this point as described above (Block 214 et seq.)

If all the detectors 26 within the detector array 14 have been queried for the current horizontal position (Block 226), the horizontal position is incremented (Block 228) and a determination is made as to whether or not the target object 10 or the radiation source 18, 18' and the detector array 14, 14' are still moving (Block 230). If the radiation source 18, 18' and the detector array 14, 14' are still moving (Block 230), 45 the detector to be queried is reset to zero (Block 210) and execution of the image generation program continues as described above (Block 212 et seq.).

If the target object 10 or the radiation source 18, 18' and the detector array 14, 14' have stopped moving (e.g., because they have reached the farthest point of travel down the tracks or the mobile system path or the target object path (Block 230)), execution of the image generation program is terminated (Block 232).

Figure 10:
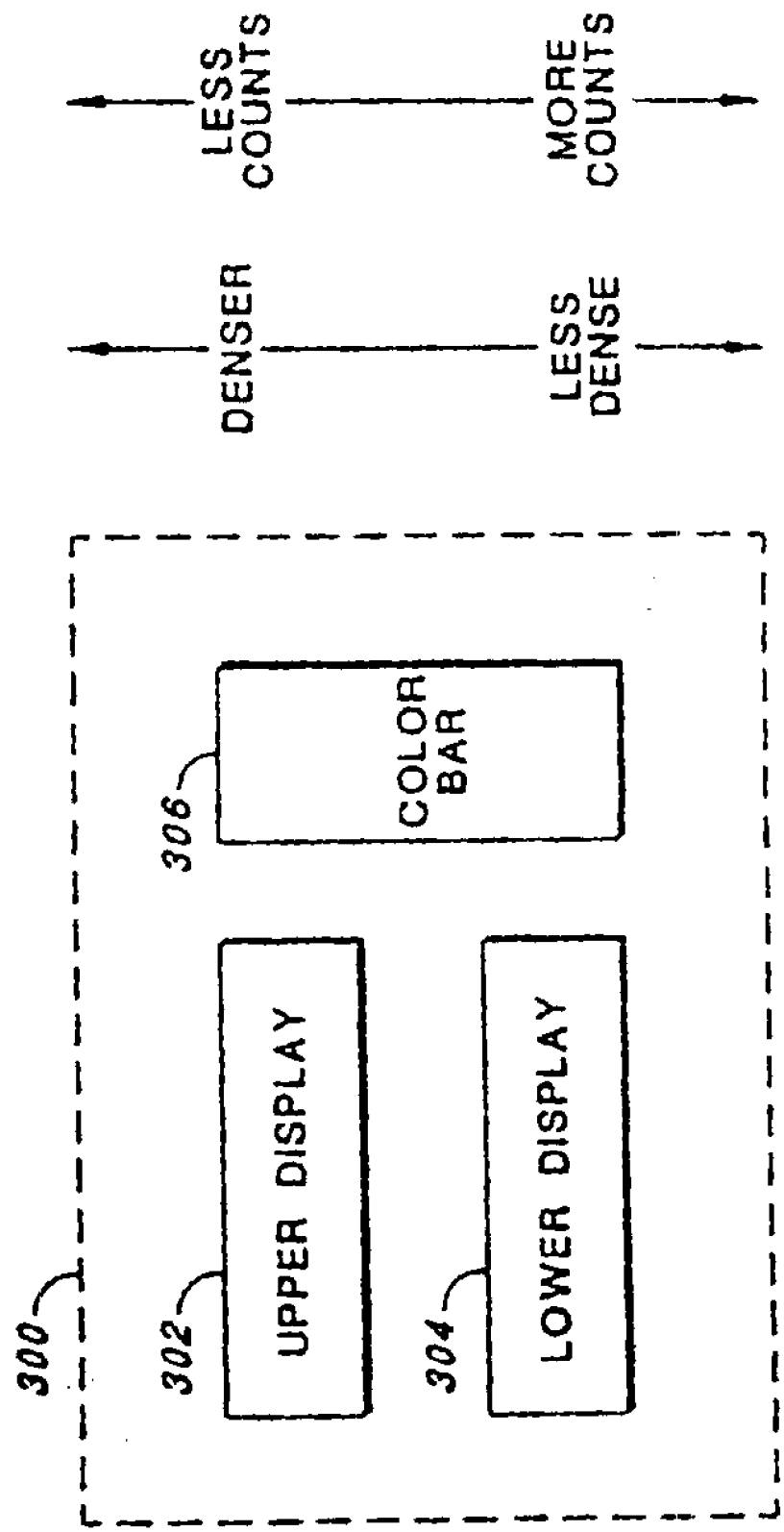
FIG. 10 is a diagram illustrating a preferred screen layout for the image displayed on the display device of FIGS. 1 and 2.

Referring next to FIG. 10, a diagram is shown illustrating a preferred screen layout for the images displayed on the display device of FIG. 4.

As shown, the screen display 300 is divided into an upper display 302, a lower display 304 and a color bar 306. In accordance with the present embodiment, the upper display 302 can be used, as mentioned above, to display images stored on disk. These images will generally be reference images used for visual comparison with an image representative of a vehicle under inspection. The lower display 304, in addition to being able to display images stored on disk, is used to display images, as they are generated, indicative of the various densities within the vehicle under inspection. Both the upper and lower displays 302, 304 are color mapped using the current color map, gain and offset, so that they can be visually compared to one another.

Any differences in a reference image, and an image generated during inspection of a vehicle may indicate the presence of contraband within the vehicle under inspection.

The color bar 306 indicates the colors that are mapped to the various densities detectable by the present embodiment, serving as a reference to the operator as to which colors indicate higher densities than others. As suggested in FIG. 10, colors nearer to the top of the color bar 306 are indicative of more density, i.e., fewer photons counted as penetrating the vehicle under inspection, and colors nearer to the bottom of the color bar 306 are indicative of less density, i.e., more photons counted as penetrating the vehicle under inspection.

Thus, a system and associated methods are provided in the present embodiment for determining the densities within a vehicle under inspection based on discrete photon counting, and for generating an image indicative of such densities. Advantageously, such determination is made based on discrete photon counting, thereby eliminating the need for high levels of gamma-ray or x-ray radiation.

The present embodiment, thus, eliminates the need to stop and manually inspect vehicles at border crossings, and other inspection points. In addition, the present embodiment, because of the very low levels or gamma-ray or x-ray radiation, advantageously eliminates the need to stop and evacuate the vehicle before it is subjected to very high strength gamma-ray or x-ray radiation, when the radiation source shutter opens just after the driver has passed: The scattered radiation dosage to the driver is very low, and of an acceptably minute level. Advantageously, one variation the present embodiment provides for the determination of densities within the vehicle without the need even to stop the vehicle, such as a train. Slightly higher radiation levels may, in accordance with this variation, be used to reduce or even eliminate the slowing needed to determine the densities within a vehicle, and to generate an image indicative thereof, if the radiation source is closed when the driver is "in the beam."

While the invention herein disclosed has been described by means of specific embodiments and applications thereof, numerous modifications and variations could be made thereto by those skilled in the art without departing from the scope of the invention set forth in the claims.

What is claimed is:

1. A linear detector array system for use in a target inspection system for detecting a contents of the target, the linear detector array comprising:

a plurality of vertical rows of staggered detectors including a center vertical row of staggered detectors and one or more side vertical rows of staggered detectors, each of the plurality of vertical rows being vertically staggered from each other vertical row, such that a pitch between any two closest adjacent staggered detectors is smaller than a diameter of the staggered detectors;

a processor comprising an image-generating program, the processor receiving data from each of the one or more side vertical rows and from the center vertical row;

the image-generating program further including:

adjustment means for determining an adjustment for a horizontal displacement k of the one or more side vertical rows from the center vertical row, wherein the adjustment is used to correlate the data from the side vertical rows with data from the center vertical row so as to form undistorted images for multiple planes within the target; and computing means for determining an image adjustment distance l for multiple planes within the target according to a relationship $l=kZ/D$, wherein Z is variable and is a distance between a radiation source and each of the multiple planes within the target, and wherein D is a distance between the radiation source and the linear detector array.

2. A method for processing staggered detection data for use in a target inspection system, the method comprising the steps of:

providing a plurality of vertical rows of staggered detectors, each of the plurality of vertical rows being vertically staggered from each other vertical row, such that a pitch between any two closest adjacent staggered detectors is smaller than a diameter of the staggered detectors including:

providing a center vertical row of staggered detectors;

providing one or more side vertical rows of staggered detectors;

providing a processor comprising an image-generating program;

receiving data at the processor from each of the one or more side vertical rows and from the center vertical row;

determining an adjustment for a horizontal displacement k of the one or more side vertical rows in order to correlate the data from the side vertical rows with data from the center vertical row so as to form undistorted images for multiple planes within the target; and determining an image adjustment distance l for multiple planes within the target according to a relationship $l=kZ/D$, wherein Z is variable and is a distance between a radiation source and each of the multiple planes within the target, and wherein D is a distance between the radiation source and the linear detector array.

3. The method of claim 2, further comprising:

adjusting the data from the one or more side vertical rows and the center vertical row using the adjustment distance l for each of the multiple planes to form undistorted images for each of the multiple rows; and comparing the undistorted images for each of the multiple planes to determine the location of an object within the target.

* * * * *

UNITED STATES PATENT AND TRADEMARK OFFICE
CERTIFICATE OF CORRECTION

| | |
|---|---|
| PATENT NO. | : 7,045,787 B1 |
| APPLICATION NO. | : 09/925009 |
| DATED | : May 16, 2006 |
| INVENTOR(S) | : Victor Verbinski et al. |

It is certified that error appears in the above-identified patent and that said Letters Patent is hereby corrected as shown below:

Title Page

RELATED U.S. APPLICATION DATA (63) -

In Line 4 of Section (63), please change "1997, now abandoned, which is a continuation-in-part of" to -- 1997, now abandoned, which is a continuation of --.

IN REFERENCES CITED (56) - OTHER PUBLICATIONS -

In Page 2, Column, Line 1 of the Fourth Reference, please change "Richardson, Rex D., Verbinski, Victor V. and Orphan, Victor" to -- Richardson, Rex D., Verbinski, Victor V. and Orphan, Victor --.

In Page 3, Column 2, Line 1 of the Third reference, please change "SAIC: News Release dated Jun. 17, 2004, http:www.saic." to -- SAIC: News Release dated Jun. 17, 2004, http:www.saic. --.

In Page 3, Column 2, Line 1 of the Fourth Reference, please change "SAIC: News Release dated Aug. 25, 2004, http://www.saic." to -- SAIC: News Release dated Aug. 25, 2001, http://www.saic. --.

In Page 3, Column 2, Line 1 of the Fifth Reference, please change "SAIC: News Release dated Oct. 20, 1999, http://www.saic." to --SAIC: News Release dated oct. 20, 1999, http://www.saic. --.

In Page 3, Column 2, Line 3 of the Eighth Reference, please change "jor_upgrade for port security.html (2 pp.)" to -- jor_upgrade_for_port_security.html (2 pp.) --.

In Page 3, Column 2, Line 2 of the Twelfth Reference, please change "fight terrorism," http://seattlepl.nwsource.com/printer2/in-" to -- fight terrorism, " http://seattlepi.nwsource.com/printer2/in- --.

In Page 3, Column 2, Line 3 of the Fifteenth Reference, please change "from the Internet: http://www.saic.com/products/security/" to -- from the Internet: http://www.saic.com/products/security/portal-vacis/--.

UNITED STATES PATENT AND TRADEMARK OFFICE
CERTIFICATE OF CORRECTION

PATENT NO. : 7,045,787 B1
APPLICATION NO. : 09/925009
DATED : May 16, 2006
INVENTOR(S) : Victor Verbinski et al.

It is certified that error appears in the above-identified patent and that said Letters Patent is hereby corrected as shown below:

IN THE REFERENCES CITED (56) - OTHER PUBLICATIONS CONT'D. -

In Page 3, Column 2, Line 3 of the Sixteenth References, please change "from the Internet." to -- from the Internet: http://www.saic.com/products/security/rr-vacis/railroad-tech.html. --

In Page 3, Column 2, Line 3 of the Ninteenth Reference, please change "[online ], Jun. 17, 2004 [retrieved on Jul. 8, 2004], 2 pp.," to -- [online], Jun. 17, 2004 [retrieved on Jul. 8, 2004], 2 pp., --

In Page 4, Column 1, Line 5 of the Fourth Reference, please change "jul99/news/07-26-99.html." to -- jul99/news07-26-99.html. --

In Page 4, Column 1, Line 4 of the Seventh reference, please change "cis/index/index.html." to -- cis/index.html. --

In Page 4, Column 1, Line 3 of the Ninth Reference, please change "Internet: http://www.saic.com/products/security/rr-vasic/in-" to -- Internet: http://www.saic.com/products/security/rr-vacis/in--

In Page 4, Column 1, Line 1 of the Tenth Reference, please change "Relocatable VASICR Inspection System, Overview" [on-" to -- "Relocatable VACISR Inspection System, Overview" [on- --

In Page 4, Column 2, Line 1 of the Eleventh Reference, please change "Thomas Pumps & Compresors, "WOB-LRPiston, Pumps" to -- Thomas Pumps & Compressors. "WOB-LR Piston, Pumps --

In Page 4, Column 2, Line 2 of the Twelfth Reference, please change "Applications International Corporation,." to -- Applications International Corporation, Docket 2:04-cv-02936-GPS-FMO (as of 1/10/05). --

In Page 4, Column 2, Line 4 of the Seventeenth Reference, please change "ton, Masachusetts, SPIE vol. 3575, pp. 368-374, Nov. 1998." to -- ton, Massachusetts, SPIE, vol. 3575, pp. 368-374, Nov. 1998. --

UNITED STATES PATENT AND TRADEMARK OFFICE
CERTIFICATE OF CORRECTION

| | |
|---|---|
| PATENT NO. | : 7,045,787 B1 |
| APPLICATION NO. | : 09/925009 |
| DATED | : May 16, 2006 |
| INVENTOR(S) | : Victor Verbinski et al. |

It is certified that error appears in the above-identified patent and that said Letters Patent is hereby corrected as shown below:

IN THE REFERENCES CITED (56) - OTHER PUBLICATIONS CONT'D. -

In Page 4, Column 1, Line 3 of the Second Reference, please change "Tactical Technologies and Wide Area Surveilance Interna-" to -- Tactical Technologies and Wide Area Surveillance Interna- --

In Page 5, Column 1, Lines 2 and 3 of the Third Reference, please change "Detector for Empty Liquid Transport Containers, "Technical vol., Submitted to: Executive Office of the President, In" to -- Detector for Empty Liquid Transport Containers," Technical Volume, Submitted to: Executive Office of the President, In --

Signed and Sealed this

Twenty-ninth Day of August, 2006

JON W. DUDAS
*Director of the United States Patent and Trademark Office*